(12) United States Patent
Kobayashi et al.

(10) Patent No.: US 10,022,055 B2
(45) Date of Patent: Jul. 17, 2018

(54) BLOOD PRESSURE INFORMATION MEASUREMENT DEVICE CUFF AND BLOOD PRESSURE INFORMATION MEASUREMENT DEVICE PROVIDED THEREWITH

(71) Applicants: Tatsuya Kobayashi, Otsu (JP); Kenji Fujii, Kyoto (JP); Yukiya Sawanoi, Nara (JP); Naoto Akiyama, Moriguchi (JP)

(72) Inventors: Tatsuya Kobayashi, Otsu (JP); Kenji Fujii, Kyoto (JP); Yukiya Sawanoi, Nara (JP); Naoto Akiyama, Moriguchi (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1412 days.

(21) Appl. No.: 13/632,876

(22) Filed: Oct. 1, 2012

(65) Prior Publication Data
US 2013/0060153 A1    Mar. 7, 2013

Related U.S. Application Data

(63) Continuation of application No. PCT/JP2011/052393, filed on Feb. 4, 2011.

(30) Foreign Application Priority Data

Mar. 30, 2010    (JP) .................................. 2010-077950

(51) Int. Cl.
*A61B 5/021*    (2006.01)
*A61B 5/022*    (2006.01)

(52) U.S. Cl.
CPC ...... *A61B 5/02233* (2013.01); *A61B 5/02225* (2013.01)

(58) Field of Classification Search
CPC .............. A61B 5/02233; A61B 17/132; A61B 5/02225; A61B 5/022
See application file for complete search history.

(56) References Cited

U.S. PATENT DOCUMENTS 4,406,281 A * 9/1983 Hubbard ................ A61B 46/27
128/846
5,193,549 A * 3/1993 Bellin ................ A61B 5/02233
128/DIG. 20

(Continued)

FOREIGN PATENT DOCUMENTS

JP    2000-079101 A    3/2000
JP    2005-185295 A    7/2005

(Continued)

OTHER PUBLICATIONS

International Search Report issued in corresponding International Application No. PCT/JP2011/052393 dated Mar. 15, 2011 and English translation thereof (3 pages).

(Continued)

*Primary Examiner* — Tiffany Weston
*Assistant Examiner* — Tho Tran
(74) *Attorney, Agent, or Firm* — Osha Liang LLP

(57) ABSTRACT

A blood pressure information measurement device cuff includes a wide blood pressure value measurement air bladder wrapped around a fitting area when in a fitted state, and a narrow pulse wave measurement air bladder disposed so as to be closer to the fitting area than the blood pressure value measurement air bladder when in the fitted state, and covered by the blood pressure value measurement air bladder when wrapped around the fitting area. The pulse wave measurement air bladder includes an anchored portion anchored to the blood pressure value measurement air bladder so as to be immobile relative to the blood pressure value measurement air bladder and a mobile portion that is (Continued)

not anchored to the blood pressure value measurement air bladder so as to be mobile relative to the blood pressure value measurement air bladder along a wrapping direction in which the cuff is wrapped around the measurement area.

13 Claims, 15 Drawing Sheets

(56) References Cited

U.S. PATENT DOCUMENTS

| | | | | |
|---|---|---|---|---|
| 5,660,182 | A * | 8/1997 | Kuroshaki | A61B 5/02233 600/499 |
| 6,478,745 | B2 * | 11/2002 | Nakagawa | A61B 5/021 600/499 |
| 8,430,822 | B2 * | 4/2013 | Inoue | A61B 5/02116 600/490 |
| 8,579,826 | B2 * | 11/2013 | Kobayashi | A61B 5/02007 600/483 |
| 2004/0024325 | A1 * | 2/2004 | Nishibayashi | A61B 5/02225 600/492 |
| 2004/0181254 | A1 * | 9/2004 | Choi | A61B 5/02233 606/202 |
| 2005/0182331 | A1 * | 8/2005 | Millay | A61B 5/02233 600/499 |
| 2009/0062668 | A1 | 3/2009 | Todokoro et al. | |
| 2010/0106031 | A1 | 4/2010 | Souma | |
| 2010/0137725 | A1 | 6/2010 | Takahashi et al. | |
| 2010/0298724 | A1 * | 11/2010 | Vivenzio | A61B 5/02233 600/490 |

FOREIGN PATENT DOCUMENTS

| | | |
|---|---|---|
| JP | 2006-081667 A | 3/2006 |
| JP | 2006-081668 A | 3/2006 |
| JP | 2007-044362 A | 2/2007 |
| JP | 2008-099944 A | 5/2008 |
| JP | 2008-307181 A | 12/2008 |
| JP | 2009-072548 A | 4/2009 |
| WO | 2008/044491 A1 | 4/2008 |
| WO | 2008/090811 A1 | 7/2008 |

OTHER PUBLICATIONS

Patent Abstracts of Japan, Publication No. 2000-079101, Published on Mar. 21, 2000, 1 page.
Patent Abstracts of Japan, Publication No. 2005-185295, Published on Jul. 14, 2005, 1 page.
Patent Abstracts of Japan, Publication No. 2007-044362, Published on Feb. 22, 2007, 1 page.
Patent Abstracts of Japan, Publication No. 2008-307181, Published on Dec. 25, 2008, 1 page.
Patent Abstracts of Japan, Publication No. 2006-081667, Published on Mar. 30, 2006, 1 page.
Patent Abstracts of Japan, Publication No. 2006-081668, Published on Mar. 30, 2006, 1 page.
Patent Abstracts of Japan, Publication No. 2008-099944, Published on May 1, 2008, 1 page.
Patent Abstracts of Japan, Publication No. 2009-072548, Published on Apr. 9, 2009, 1 page.

* cited by examiner

BLOOD PRESSURE INFORMATION MEASUREMENT DEVICE CUFF AND BLOOD PRESSURE INFORMATION MEASUREMENT DEVICE PROVIDED THEREWITH

TECHNICAL FIELD

The present invention relates to blood pressure information measurement device cuffs used by being wrapped around a measurement area of a body in order to measure blood pressure information, and to blood pressure information measurement devices provided therewith; the present invention particularly relates to blood pressure information measurement devices configured so as to be capable of obtaining a pulse wave as blood pressure information, and to blood pressure information measurement device cuffs provided therein.

BACKGROUND ART

Measuring the blood pressure information of a measurement subject is extremely important in understanding the health of the measurement subject. In recent years, attempts are being made to measure stress on the heart, hardening of the arteries, and so on by measuring pulse waves of measurement subjects, as opposed to simply measuring the systolic blood pressure value ("maximum blood pressure", hereinafter) and the diastolic blood pressure value ("minimum blood pressure", hereinafter), the usefulness of which as a representative index of health management is widely accepted at present. Blood pressure information measurement devices are devices for measuring such blood pressure information, and such devices are expected to have a further role in the early detection, prevention, and treatment of circulatory system conditions. Note that various types of circulatory system information generally fall under the umbrella of "blood pressure information", including such various indexes as the systolic blood pressure value, diastolic blood pressure value, average blood pressure value, pulse wave, pulse beat, artery hardness, and so on.

Generally speaking, a blood pressure information measurement device cuff (called simply a "cuff" hereinafter) is used in the measurement of blood pressure information. Here, "cuff" refers to a band-shaped or ring-shaped structure that includes a fluid bladder having an inner cavity and that can be wrapped around part of a body, and that is used to measure blood pressure information by injecting a fluid such as air, a liquid, or the like into the inner cavity and inflating or deflating the fluid bladder. In particular, cuffs that are used by being wrapped around the arm are sometimes called "manchettes".

Normally, an air bladder, formed in a bladder shape by layering comparatively flexible sheet-shaped members configured of a resin or the like and connecting the edges thereof, is used as the fluid bladder contained within the cuff. Because this air bladder is configured of a comparatively flexible member as mentioned here, there is a tendency for wrinkles to appear with ease in the surface of the air bladder when the cuff is wrapped around the measurement area.

The appearance of wrinkles in the air bladder causes the skin to be pinched by the wrinkles and blood stasis to occur, sudden pressure fluctuations to occur due to the wrinkles suddenly disappearing or receding when the air bladder is being inflated/deflated, and so on, and the precision with which the blood pressure information is measured to be negatively influenced. Furthermore, the appearance of a deep wrinkle in the air bladder causes the fitting area of the cuff to be unevenly pressurized, the wrinkle to interfere with the flow of air within the air bladder, and the artery to not be sufficiently pressurized, and so on. Further still, because there are individual variations in the fitting area for the cuff, wrinkles will appear with varying frequency due to such differences in the shape of the fitting area (primarily differences in the circumferential length, differences in the curvature factor, and so on); the appearance of wrinkles will then result in variations in the measurement precision.

A cuff configured so as to include two or more air bladders has been proposed for the purpose of more precisely measuring a pulse wave and obtaining an index or the like indicating a blood pressure value, artery hardness, or the like. JP-2000-79101A (Patent Citation 1), JP-2005-185295A (Patent Citation 2), JP-2007-44362A (Patent Citation 3), JP-2008-307181A (Patent Citation 4), and so on are known as literature disclosing a cuff configured so as to include two or more air bladders.

With a cuff that includes two air bladders as disclosed in these pieces of literature, the configuration that is mainly employed has a low-capacity air bladder used for pulse wave measurement being covered by a high-capacity air bladder used to block the blood in order to measure a pulse wave with a high level of precision. Wrinkles appearing in the low-capacity air bladder used for pulse wave measurement may occur in a cuff having such a configuration. The wrinkles that appear in the surface of the low-capacity air bladder will have an extremely high degree of influence on the blood pressure information measurement precision as described above, meaning that the original purpose of measuring a pulse wave at a higher level of precision will not be achieved. Therefore, when employing a cuff having such a configuration, it is absolutely necessary to make improvements for effectively suppressing the appearance of wrinkles in the surface of the low-capacity air bladder used for pulse wave measurement.

Meanwhile, JP-2006-81667A (Patent Citation 5), JP-2006-81668A (Patent Citation 6), JP-2008-99944A (Patent Citation 7), and so on can be given as examples of literature disclosing a cuff configured so as to be capable of suppressing the appearance of wrinkles in an air bladder.

With the cuff disclosed in the stated JP-2006-81667A, the configuration is such that a band-shaped member extending along the direction in which the cuff is wrapped is disposed within the air bladder, and the appearance of wrinkles is suppressed by forming an air flow channel along both sides of the band-shaped member in the width direction thereof.

Meanwhile, with the cuff disclosed in the stated JP-2006-81668A, the configuration is such that a breathable member configured of a sponge or the like is disposed within the air bladder, and the appearance of wrinkles is suppressed by securing air flow channels within the air bladder using the air passages that are formed within the breathable member.

Furthermore, with the cuff disclosed in the stated JP-2008-99944A, the configuration is such that a sliding sheet serving as a low-friction member is disposed between an outer cover that encloses the air bladder and the surface of the air bladder that pressurizes the body, and the appearance of wrinkles is suppressed by making it easier for the air bladder to slide upon the sliding sheet.

Patent Citation 1: JP-2000-79101A
Patent Citation 2: JP-2005-185295A
Patent Citation 3: JP-2007-44362A
Patent Citation 4: JP-2008-307181A
Patent Citation 5: JP-2006-81667A
Patent Citation 6: P-2006-81668A
Patent Citation 7: JP-2008-99944A

SUMMARY OF INVENTION

However, even in the case where a configuration such as that disclosed in the aforementioned JP-2006-81667A, JP-2006-81668A, and JP-2008-99944A is employed, it is necessary to additionally provide a sponge, a band-shaped member, or a sliding sheet in the cuff, in addition to the air bladder and an outer cover. These additions complicate the structure and increase the number of components, and also lead to an increase in the manufacturing costs. Such adverse effects are also apparent in the aforementioned cuffs configured so as to have two air bladders in a layered state.

Therefore, one or more embodiments of the present invention provide a blood pressure information measurement device cuff having a simple configuration capable of effectively suppressing the appearance of wrinkles in the surface of a low-capacity fluid bladder, and provide a blood pressure information measurement device that includes such a cuff.

A blood pressure information measurement device cuff according to one or more embodiments of the present invention takes on a ring-shaped state when wrapped around a fitting area in a fitted state, and includes a wide first fluid bladder that is wrapped around the fitting area when in the fitted state, and a narrow second fluid bladder disposed so as to be closer to the fitting area than the first fluid bladder when in the fitted state and that is covered by the first fluid bladder when wrapped around the fitting area; the second fluid bladder includes an anchored portion that is anchored to the first fluid bladder so as to be immobile relative to the first fluid bladder and a mobile portion that is not anchored to the first fluid bladder so as to be mobile relative to the first fluid bladder along a wrapping direction in which the cuff is wrapped around the measurement area.

In the stated blood pressure information measurement device cuff according to one or more embodiments of the present invention, the first fluid bladder is, when in the fitted state, wrapped around an area closer to the heart within the fitting area and an area away from the heart within the fitting area; and the second fluid bladder is, when in the fitted state, wrapped around only the area closer to the heart within the fitting area.

The stated blood pressure information measurement device cuff according to one or more embodiments of the present invention further includes a guidance portion that guides the movement of the mobile portion along the wrapping direction.

The stated blood pressure information measurement device cuff according to one or more embodiments of the present invention further includes a vibration blocking portion, disposed between the first fluid bladder and the second fluid bladder, that prevents vibrations produced in the first fluid bladder from being transmitted to the second fluid bladder and that prevents vibrations produced in the second fluid bladder from being transmitted to the first fluid bladder.

The stated blood pressure information measurement device cuff according to one or more embodiments of the present invention further includes a guidance member for guiding the movement of the mobile portion along the wrapping direction, and a vibration blocking member, disposed between the first fluid bladder and the second fluid bladder, that prevents vibrations produced in the first fluid bladder from being transmitted to the second fluid bladder and that prevents vibrations produced in the second fluid bladder from being transmitted to the first fluid bladder. In this case, according to one or more embodiments of the present invention, the guidance member and the vibration blocking member are both configured of a nonwoven material formed into a band shape; and the vibration blocking member is disposed between the first fluid bladder and the second fluid bladder and is anchored to the first fluid bladder, the guidance member is overlaid upon the vibration blocking member so as to cover at least part of the second fluid bladder and is anchored to the vibration blocking member, and the movement of the mobile portion along the wrapping direction is guided by inserting at least part of the mobile portion into a channel defined by the vibration blocking member and the guidance member.

In the stated blood pressure information measurement device cuff according to one or more embodiments of the present invention, the entirety of the mobile portion may be inserted into the channel.

In the stated blood pressure information measurement device cuff according to one or more embodiments of the present invention, the end of the mobile portion located on the opposite side as the anchored portion may be disposed having been led out from the channel.

In the stated blood pressure information measurement device cuff according to one or more embodiments of the present invention, the anchored portion is formed by anchoring one end of the second fluid bladder to the first fluid bladder via the vibration blocking member.

In the stated blood pressure information measurement device cuff according to one or more embodiments of the present invention, the anchoring of the vibration blocking member to the first fluid bladder, the anchoring of the guidance member to the vibration blocking member, and the anchoring of the second fluid bladder to the vibration blocking member is all carried out through welding.

In the stated blood pressure information measurement device cuff according to one or more embodiments of the present invention, the anchored portion is located at one end of the second fluid bladder in the lengthwise direction thereof.

The stated blood pressure information measurement device cuff according to one or more embodiments of the present invention further includes an outer cover that contains the first fluid bladder and the second fluid bladder. According to one or more embodiments of the present invention, of the two ends of the outer cover in the wrapping direction, the anchored portion is disposed on the end that is located toward the fitting area when the cuff is in the fitted state.

In the stated blood pressure information measurement device cuff according to one or more embodiments of the present invention, the anchored portion is located in approximately the center of the second fluid bladder in the lengthwise direction thereof.

A blood pressure information measurement device according to one or more embodiments of the present invention includes one of the blood pressure information measurement device cuffs described above.

According to one or more embodiments of the present invention, it is possible to provide a blood pressure information measurement device cuff and a blood pressure information measurement device including such a cuff that are capable of effectively suppressing the appearance of wrinkles in the surface of a low-capacity fluid bladder using a simple configuration.

BRIEF DESCRIPTION OF DRAWINGS

FIG. 8A is a schematic cross-sectional view of the cuff before wrapping, whereas FIG. 8B is a schematic cross-sectional view of the cuff during the wrapping process.

FIG. 9A is a schematic cross-sectional view of the cuff before wrapping according to a comparative example, whereas FIG. 9B is a schematic cross-sectional view of the cuff during the wrapping process according to a comparative example.

DETAILED DESCRIPTION OF INVENTION

Figure 1:
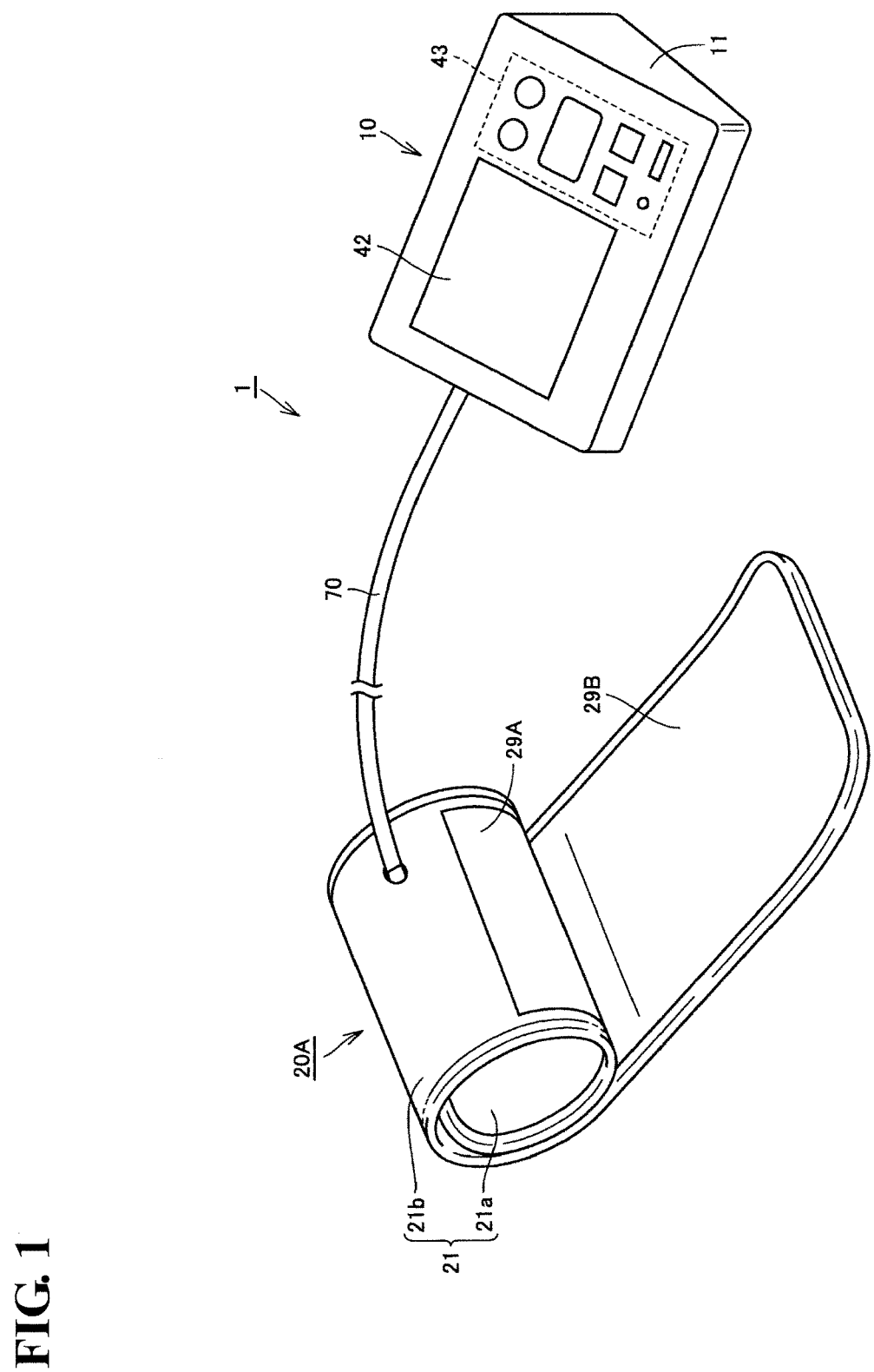
FIG. 1 is a perspective view illustrating the external structure of a blood pressure information measurement device according to a first embodiment of the present invention.

Hereinafter, embodiments of the present invention will be described in detail with reference to the drawings. In the following first and second embodiments and the variations thereon, a blood pressure information measurement device provided with both a function for obtaining and displaying blood pressure values, such as a maximum blood pressure and a minimum blood pressure, and a function for obtaining and displaying an index indicating artery hardness by detecting a pulse wave will be described as an example of a blood pressure information measurement device in which one or more embodiments of the present invention is applied. Note that in the embodiments and variations thereon described below, identical or corresponding constituent elements are assigned the same reference numerals in the drawings, and individual descriptions thereof will not be repeated.

First Embodiment

Figure 2:
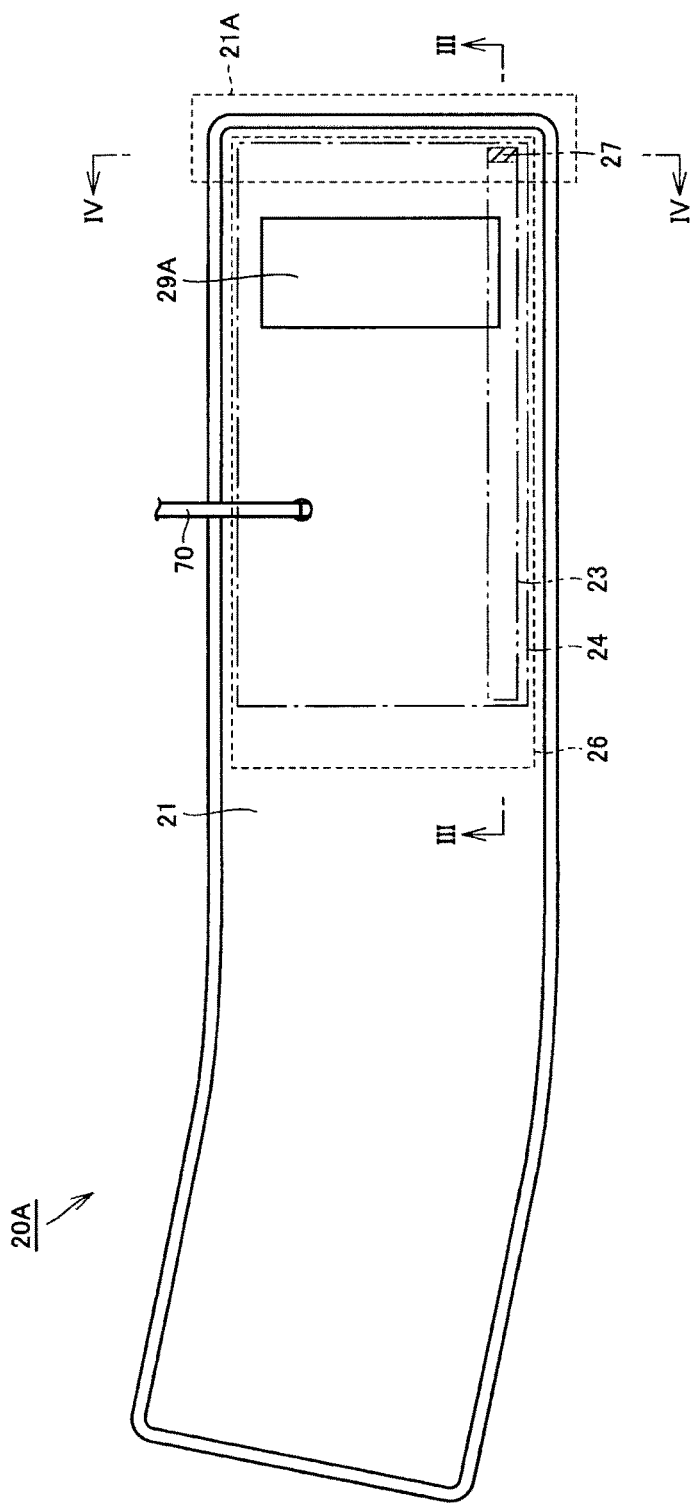
FIG. 2 is a diagram illustrating a blood pressure information measurement device cuff according to the first embodiment of the present invention in an unwrapped state, as seen from the outer circumferential surface thereof.
Figure 3:
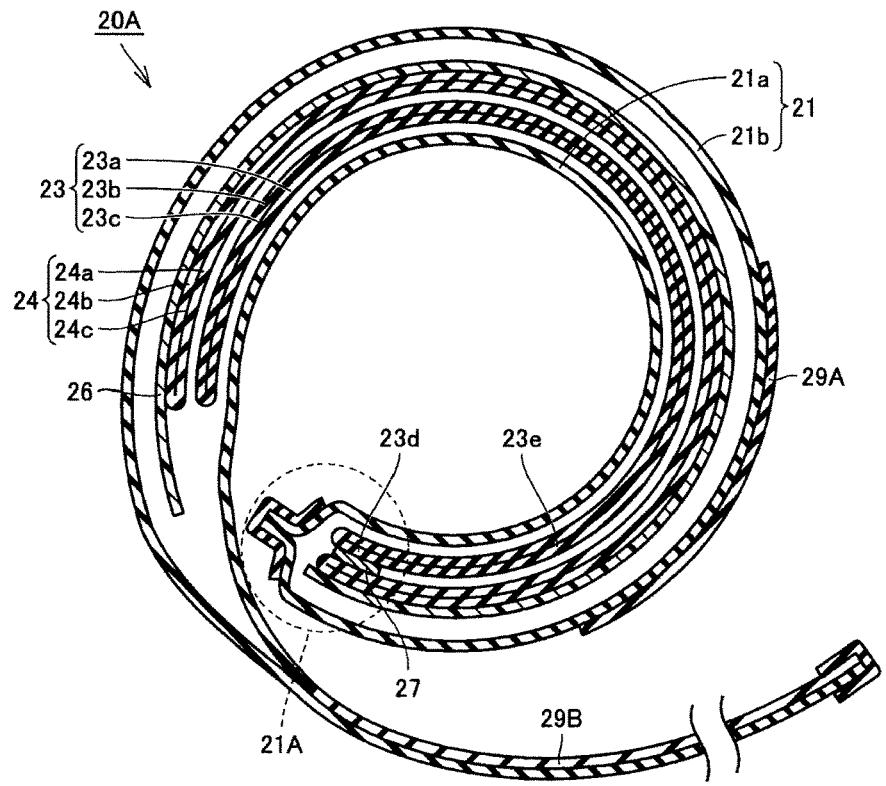
FIG. 3 is a cross-sectional view illustrating the blood pressure information measurement device cuff according to the first embodiment of the present invention from a plane orthogonal to the axial direction of the cuff (that is, a cross-sectional view following the line shown in FIG. 2).
Figure 4:
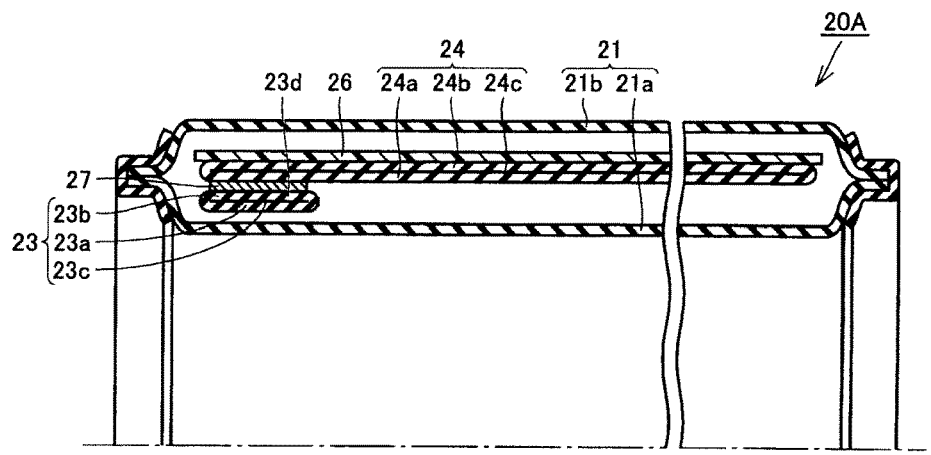
FIG. 4 is a cross-sectional view illustrating the blood pressure information measurement device cuff according to the first embodiment of the present invention from a plane parallel to the axial direction of the cuff (that is, a cross-sectional view following the IV-IV line shown in FIG. 2).

FIG. 1 is a perspective view illustrating the external structure of a blood pressure information measurement device according to a first embodiment of the present invention, whereas FIG. 2 is a diagram illustrating a cuff shown in FIG. 1 in an unwrapped state, as seen from the outer circumferential surface thereof. FIG. 3, meanwhile, is a cross-sectional view illustrating a plane orthogonal to the axial direction of the cuff shown in FIG. 1, whereas FIG. 4 is a cross-sectional view illustrating a plane parallel to the axial direction of the cuff shown in FIG. 1. Here, the cross-sections in FIG. 3 and FIG. 4 are cross-sections that include a pulse wave measurement air bladder, and show cross-sections taken along the line and the IV-IV line, respectively, of the unwrapped cuff shown in FIG. 2. First, the blood pressure information measurement device and the structure of the blood pressure information measurement device cuff provided in the device according to the present embodiment will be described with reference to FIGS. 1 through 4.

As shown in FIG. 1, a blood pressure information measurement device 1 according to the present embodiment includes a main unit 10, a cuff 20A, and an air tube 70. The main unit 10 includes a box-shaped casing 11, and a display unit 42 and an operating unit 43 are provided on the top surface thereof. During measurement, the main unit 10 is used by being placed on a placement surface such as a table or the like. The cuff 20A has a band shaped that is capable of being wrapped around an upper arm, which serves as a fitting area, and is covered by an outer cover 21 that serves as an external sheathing. During measurement, the cuff 20A is used by being wrapped around and worn on the upper arm. Note that the air tube 70 connects the main unit 10 and the cuff 20A, which are configured as separate units, and is configured of a flexible tube.

As shown in FIGS. 2 through 4, the cuff 20A primarily includes the aforementioned outer cover 21, a high-capacity blood pressure value measurement air bladder 24 that serves as a first fluid bladder, a low-capacity pulse wave measurement air bladder 23 that serves as a second fluid bladder, and a curler 26 that serves as a curved elastic board.

Furthermore, as shown in FIGS. 1, 3, and 4, the outer cover 21 is formed having a bag shape by stacking and connecting (for example, stitching or welding) the edges of an inside cover 21a, which makes contact with the surface of the upper arm when the cuff 20A is wrapped around the upper arm, and an outside cover 21b, which is located furthest outward when the cuff 20A is wrapped around the upper arm. The stated pulse wave measurement air bladder 23, blood pressure value measurement air bladder 24, and curler 26 are stacked in that order from the inside and held within the space inside the outer cover 21.

Surface fasteners 29A and 29B are provided on the outer circumferential surface toward one end 21A in the lengthwise direction of the outer cover 21 (in other words, in the direction in which the cuff 20A is wrapped around the upper arm) and on the inner circumferential surface toward the other end in the lengthwise direction, respectively. Here, the surface fastener 29A is configured of, for example, a hook fastener, whereas the surface fastener 29B is configured of, for example, a loop fastener. The surface fasteners 29A and 29B are engaged when the outer cover 21 is wrapped around the upper arm and a portion of the outer cover 21 toward the stated one end 21A overlaps with a portion of the outer cover 21 toward the other end upon the surface of the upper arm. Through this, the cuff 20A is fitted and secured on the upper arm. In other words, the surface fasteners 29A and 29B correspond to a locking portion used when fitting the cuff 20A onto the upper arm.

In the outer cover 21, according to one or more embodiments of the present invention, a member that is sufficiently capable of stretching as the inside cover 21a is used, so that the pressurizing force applied to the upper arm by the inflation of the pulse wave measurement air bladder 23 and the blood pressure value measurement air bladder 24 is not inhibited by the inner cover 21a. Meanwhile, in the outer cover 21, a member that is comparatively less stretchable than the inside cover 21a is used as the outside cover 21b. In light of this, a material configured of synthetic fibers such as polyamide (PA), polyester, or the like, the stretchability of which can be adjusted relatively easily, is used as the outer cover 21.

As shown in FIGS. 3 and 4, according to one or more embodiments of the present invention, the pulse wave measurement air bladder 23 is configured of a bag-shaped member formed of a resin sheet, and includes: an inner circumferential portion 23a located on the inner side when the cuff 20A is in a fitted state; an outer circumferential portion 23b located on the outer side when the cuff 20A is in a fitted state; and an inner cavity 23c that is defined by the inner circumferential portion 23a and the outer circumferential portion 23b. The pulse wave measurement air bladder 23 can be formed in a bag shape by, for example, overlaying two resin sheets and welding the edges thereof to each other. The inner cavity 23c of the pulse wave measurement air bladder 23 is connected, via the stated air tube 70, to a pressure pump 31A and an exhaust valve 32A (mentioned later; see FIG. 5), and inflation/deflation is carried out using the pressure pump 31A and the exhaust valve 32A. Note that in order to adjust the pressure applied to the upper arm, the pulse wave measurement air bladder 23 has gussets formed on the sides thereof in the width direction.

Meanwhile, according to one or more embodiments of the present invention, the blood pressure value measurement air bladder 24 is configured of a bag-shaped member formed of a resin sheet, and includes: an inner circumferential portion 24a located on the inner side when the cuff 20A is wrapped around the upper arm; an outer circumferential portion 24b located on the outer side when the cuff 20A is wrapped around the upper arm; and an inner cavity 24c defined by the inner circumferential portion 24a and the outer circumferential portion 24b. The blood pressure value measurement air bladder 24 can be formed in a bag shape by, for example, overlaying two resin sheets and welding the edges thereof to each other. The inner cavity 24c of the blood pressure value measurement air bladder 24 is connected, via the stated air tube 70, to the pressure pump 31A and the exhaust valve 32A (mentioned later; see FIG. 5), and inflation/deflation is carried out using the pressure pump 31A and the exhaust valve 32A. Note that in order to optimize the pressure applied to the upper arm, the blood pressure value measurement air bladder 24 has gussets formed on the sides thereof in the width direction.

Note that any resin sheet material can be used to configure the pulse wave measurement air bladder 23 and the blood pressure value measurement air bladder 24 as long as the material is highly stretchable and no air leaks from the inner cavity after the welding. In light of this, according to one or more embodiments of the present invention, ethylene-vinyl acetate copolymer (EVA), polyvinyl chloride (PVC), polyurethane (PU), polyamide (PA), crude rubber, and so on can be given as examples of materials for the resin sheet.

As shown in FIGS. 2 and 4, the wide blood pressure value measurement air bladder 24 is disposed so as to be positioned spanning across essentially the entirety of the cuff 20A in the width direction. On the other hand, the narrow pulse wave measurement air bladder 23 is disposed so as to be positioned only at one end of the cuff 20A in the width direction. Here, the one end of the cuff 20A in the width direction, where the pulse wave measurement air bladder 23 is disposed, is the end located closer to the heart when the cuff 20A is in the fitted state, and therefore when the cuff 20A is in the fitted state, the pulse wave measurement air bladder 23 is wrapped around only the area closer to the heart within the upper arm, which corresponds to the fitting area. On the other hand, in the fitted state, the blood pressure value measurement air bladder 24 is wrapped spanning the entirety including both the area closer to the heart and the area away from the heart within the upper arm, which corresponds to the fitting area. Here, in the fitted state, the pulse wave measurement air bladder 23 is disposed so as to overlap with the blood pressure value measurement air bladder 24 toward the inner side of the blood pressure value measurement air bladder 24, and therefore the blood pressure value measurement air bladder 24 covers the outer side of the pulse wave measurement air bladder 23 for the stated one end in the width direction of the cuff 20A.

The pulse wave measurement air bladder 23 has a lower capacity than the blood pressure value measurement air bladder 24. According to one or more embodiments of the present invention, the air capacity of the pulse wave measurement air bladder 23 is less than ⅕ the air capacity of the blood pressure value measurement air bladder 24. For example, the size of the pulse wave measurement air bladder 23 is approximately 20 mm×200 mm, whereas the size of the blood pressure value measurement air bladder 24 is approximately 90 mm to 105 mm×200 mm.

As shown in FIGS. 2 through 4, the curler 26 is a flexible member configured so as to be capable of the elastic deformation in the radial direction when wrapped into a ring-shape, and has cuts that extend along the axial direction formed in predetermined locations in the circumferential direction. Due to these cuts, the curler 26 can elastically deform so as to extend and contract in the radial direction when an external force is applied thereto. In other words, the curler 26 deforms in the radial direction when an external force acts thereon, but returns to its original state when no external force is acting thereon. As a result, the curler 26 is configured so as to maintain its own ring-shaped form and thus follow the upper arm. The curler 26 makes it easier for the measurement subject him or herself to fit the cuff 20A onto his or her upper arm, and also biases the pulse wave measurement air bladder 23 and the blood pressure value measurement air bladder 24 toward the upper arm when the cuff 20A is wrapped around the upper arm. Note that the curler 26 is formed of a resin member such as polypropylene (PP) in order to achieve a sufficient elastic force.

Here, with the cuff 20A according to the present embodiment, one end of the pulse wave measurement air bladder 23 in the wrapping direction on the upper arm (in other words, the circumferential direction of the cuff 20A after being wrapped around the upper arm) is anchored to the blood pressure value measurement air bladder 24 via an adhesive member 27; the portion aside from the stated end is not anchored to the blood pressure value measurement air bladder 24. Accordingly, the one end of the pulse wave measurement air bladder 23 that is anchored to the blood pressure value measurement air bladder 24 via the adhesive member 27 functions as an anchored portion 23d that cannot be moved relative to the blood pressure value measurement air bladder 24, and the portion of the pulse wave measurement air bladder 23 aside from the stated end that is not anchored to the blood pressure value measurement air bladder 24 functions as a mobile portion 23e that can be moved relative to the blood pressure value measurement air bladder 24 along the aforementioned wrapping direction.

Note that of the pair of ends of the outer cover 21 in the stated wrapping direction, the stated anchored portion 23d of the pulse wave measurement air bladder 23 is disposed toward the one end 21A, which is located on the inner side when the cuff 20A is wrapped around the upper arm. Meanwhile, for example, double-sided tape, in which an adhesive layer is provided on both sides, can be used favorably as the adhesive member 27. Here, according to one or more embodiments of the present invention, the adhesive member 27 also functions as a vibration blocking member for ensuring that vibrations produced by the pulse wave measurement air bladder 23 and the blood pressure value measurement air bladder 24 are not transmitted to each other; for example, double-sided tape in which an adhesive layer is provided on both sides of a sponge material configured of a urethane sheet or the like can be used favorably as the adhesive member 27 for achieving such a function.

Figure 5:
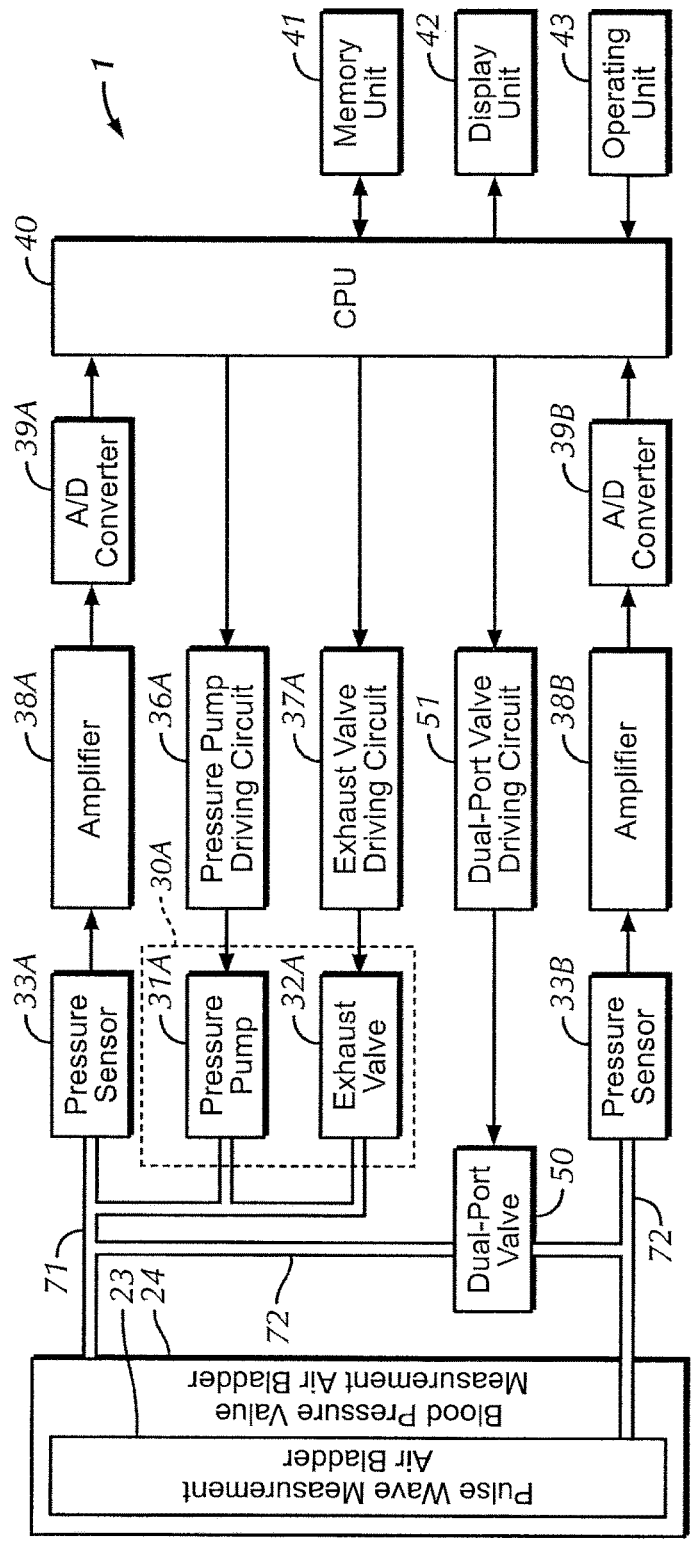
FIG. 5 is a diagram illustrating the functional block configuration of the blood pressure information measurement device according to the first embodiment of the present invention.

FIG. 5 is a diagram illustrating the functional block configuration of the blood pressure information measurement device according to the present embodiment. Next, the functional block configuration of the blood pressure information measurement device according to the present embodiment will be described with reference to FIG. 5.

As shown in FIG. 5, in addition to the aforementioned pulse wave measurement air bladder 23, blood pressure value measurement air bladder 24, display unit 42, and operating unit 43, the blood pressure information measurement device 1 according to the present embodiment includes: pressure sensors 33A and 33B; the pressure pump 31A and exhaust valve 32A serving as an inflation/deflation mechanism 30A; a central processing unit (CPU) 40 that serves as a control unit; a memory unit 41 that serves as a storage unit; a first pipe unit 71 and a second pipe unit 72 serving as pipes; and a dual-port valve 50 that serves as an opening/closing valve.

The pressure pump 31A and exhaust valve 32A serving as the inflation/deflation mechanism 30A are components for inflating/deflating the pulse wave measurement air bladder 23 and the blood pressure value measurement air bladder 24. The driving of the pressure pump 31A is controlled by a pressure pump driving circuit 36A that receives instructions from the CPU 40, and inflates the pulse wave measurement air bladder 23 and the blood pressure value measurement air bladder 24 by introducing pressurized air into the pulse wave measurement air bladder 23 and the blood pressure value measurement air bladder 24. The driving of the exhaust valve 32A, meanwhile, is controlled by an exhaust valve driving circuit 37A that receives instructions from the CPU 40; when the exhaust valve 32A is closed, the pressure in the pulse wave measurement air bladder 23 and the blood pressure value measurement air bladder 24 is maintained, whereas when the exhaust valve 32A is opened, the pulse wave measurement air bladder 23 and the blood pressure value measurement air bladder 24 are deflated by exhausting the air from within the pulse wave measurement air bladder 23 and the blood pressure value measurement air bladder 24.

The pressure sensor 33A is a pressure detection unit for detecting the internal pressure of the blood pressure value measurement air bladder 24. The pressure sensor 33A detects the internal pressure of the blood pressure value measurement air bladder 24 and outputs a signal based on the detected internal pressure to an amplifier 38A. The amplifier 38A amplifies the signal inputted from the pressure sensor 33A and outputs the amplified signal to an A/D (Analog/Digital) converter 39A. The A/D converter 39A converts the amplified signal inputted from the amplifier 38A from an analog signal into a digital signal and outputs the post-conversion digital signal to the CPU 40.

The pressure sensor 33B is a pressure detection unit for detecting the internal pressure of the pulse wave measurement air bladder 23. The pressure sensor 33B detects the internal pressure of the pulse wave measurement air bladder 23 and outputs a signal based on the detected internal pressure to an amplifier 38B. The amplifier 38B amplifies the signal inputted from the pressure sensor 33B and outputs the amplified signal to an A/D converter 39B. The A/D converter 39B converts the amplified signal inputted from the amplifier 38B from an analog signal into a digital signal and outputs the post-conversion digital signal to the CPU 40.

The first pipe unit 71 connects the blood pressure value measurement air bladder 24, the pressure pump 31A, the exhaust valve 32A, and the pressure sensor 33A. Meanwhile, the second pipe unit 72 branches from the first pipe unit 71 at a predetermined location, and connects the first pipe unit 71, the pulse wave measurement air bladder 23, and the pressure sensor 33B. As a result, the pulse wave measurement air bladder 23 is connected primarily to the pressure pump 31A and the exhaust valve 32A via the first pipe unit 71 and the second pipe unit 72, and is also connected to the pressure sensor 33B via the second pipe unit 72. Note that part of the first pipe unit 71 and second pipe unit 72 corresponds to the aforementioned air tube 70.

The dual-port valve 50 is provided at a predetermined location in the second pipe unit 72. The driving of the dual-port valve 50 is controlled by a dual-port valve driving circuit 51 that receives instructions from the CPU 40; when the dual-port valve 50 is opened, the first pipe unit 71 and the pulse wave measurement air bladder 23 communicate, whereas when the dual-port valve 50 is closed, the first pipe unit 71 and the pulse wave measurement air bladder 23 do not communicate, thus maintaining the internal pressure in the pulse wave measurement air bladder 23.

The operating unit 43 is a constituent element for accepting operations made by a user and outputting those operations to the CPU 40, and is configured of, for example, push buttons. The display unit 42 is a constituent element for displaying the operational state of the blood pressure information measurement device 1, displaying information such as blood pressure value measurement results and measurement results for artery hardness indices outputted by the CPU 40 after a measurement, and so on, and is configured of, for example, a liquid-crystal display (LCD). The memory unit 41 is a constituent element for storing programs executed by the CPU 40, storing information such as the stated measurement results, and so on, and is configured of, for example, a random access memory (RAM), a read-only memory (ROM), or the like.

The CPU 40 controls the overall operations of the blood pressure information measurement device 1, receives inputs from the operating unit 43 and the memory unit 41, and outputs various types of information to the display unit 42 and the memory unit 41. In addition, the CPU 40 accepts the input of pressure information detected by the pressure sensors 33A and 33B, and generates and outputs signals for driving the pressure pump 31A, the exhaust valve 32A, and the dual-port valve 50. Furthermore, the CPU 40 functions as a blood pressure value obtainment unit that calculates and obtains a blood pressure value based on pressure information inputted from the pressure sensor 33A as well as a pulse wave obtainment unit that detects and obtains a pulse wave based on pressure information inputted from the pressure sensor 33B; the CPU 40 also functions as an index calculation unit that calculates an index indicating an artery hardness based on the obtained pulse wave.

A known oscillometric blood pressure value calculation method or the like can be applied as the specific method by which the CPU 40 calculates the blood pressure value, and thus descriptions thereof will be omitted here. Furthermore, a known method can be applied as the specific method by which the CPU 40 calculates the index indicating the artery hardness, such as a method of calculation based on Tr (traveling time to reflected wave; also expressed as "ΔTp") for an obtained pulse wave waveform, a method of calculation based on the augmentation index (AI) of the obtained pulse wave waveform, and so on; therefore, descriptions of such a method will be omitted as well.

Figure 6:
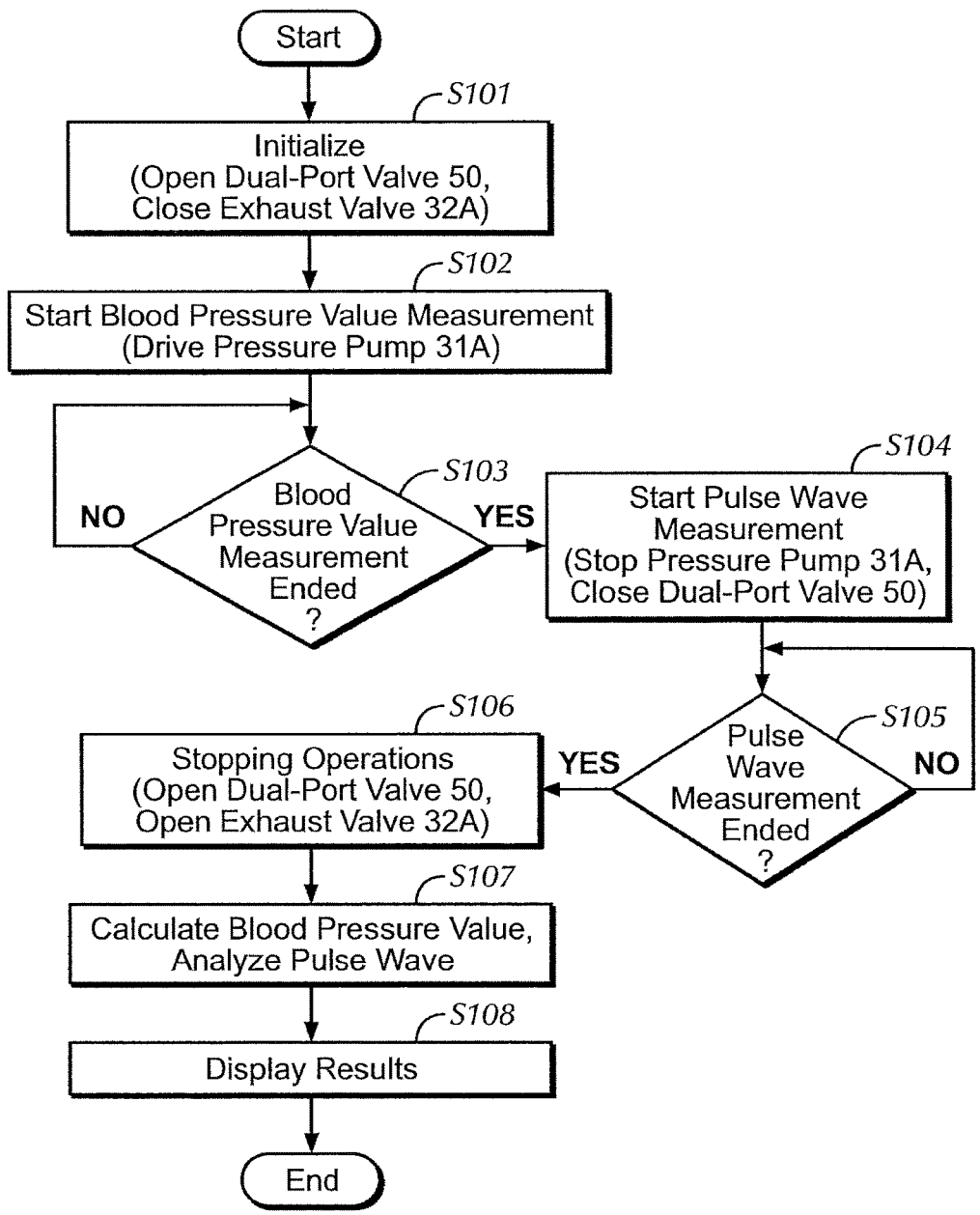
FIG. 6 is a flowchart illustrating measurement operations performed by the blood pressure information measurement device according to the first embodiment of the present invention.
Figure 7:
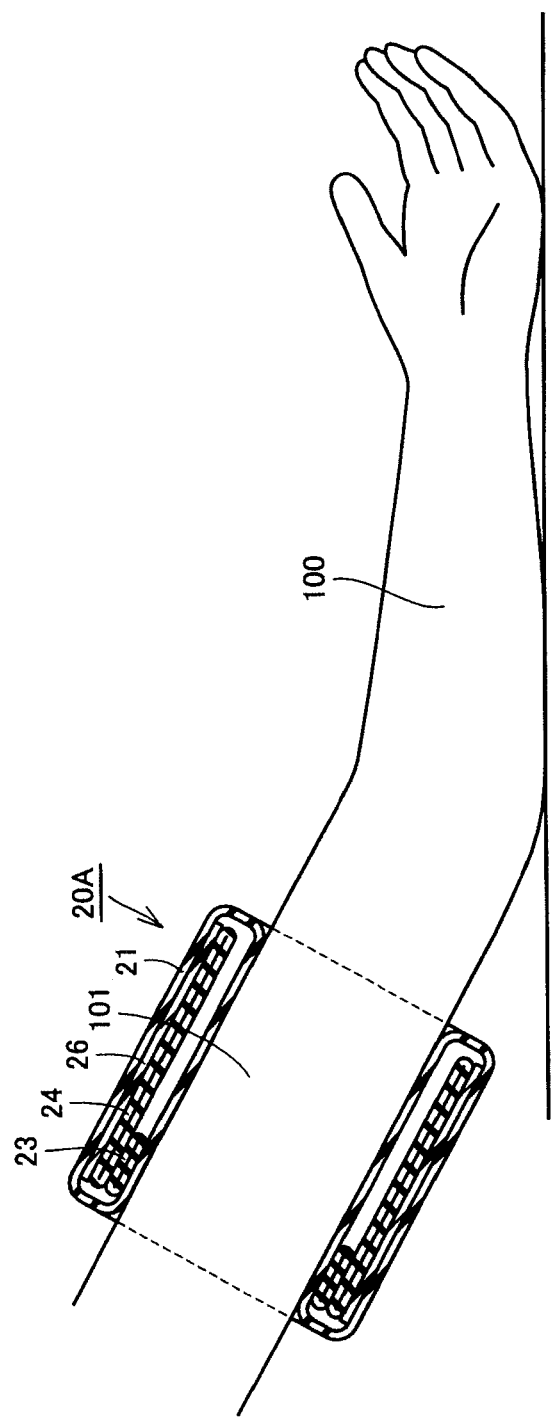
FIG. 7 is a schematic diagram illustrating a state in which the blood pressure information measurement device cuff according to the first embodiment of the present invention is wrapped around and worn on an upper arm.

FIG. 6 is a flowchart illustrating measurement operations performed by the blood pressure information measurement device according to the present embodiment. A program for executing the measurement operations illustrated in this flowchart is stored in advance in the memory unit shown in FIG. 5, and the measurement operations illustrated in the flowchart are realized by the CPU reading out the program from the memory unit and executing the program. Meanwhile, FIG. 7 is a schematic diagram illustrating a state in which the cuff illustrated in FIG. 1 is wrapped around and worn on the upper arm. Next, measurement operations performed by the blood pressure information measurement device, a state in which the cuff is worn, and so on according to the present embodiment will be described with reference to FIGS. 6 and 7.

When using the blood pressure information measurement device 1 according to the present embodiment to measure various types of blood pressure information, first, as shown in FIG. 7, the cuff 20A is fitted onto the upper arm 101 of the left arm 100 of a measurement subject. Here, as shown in FIG. 7, the cuff 20A is fitted so that the pulse wave measurement air bladder 23 is positioned in the side closer to the heart within the fitting area for the cuff 20A, and the cuff 20A is wrapped so as to follow the circumferential direction of the upper arm 101 and is securely anchored using the surface fasteners 29A and 29B provided in the outer cover 21. Next, the blood pressure information measurement device 1 commences the measurement operations when the measurement subject or the like operates the operating unit 43 in the main unit 10.

As shown in FIG. 6, when the CPU 40 receives an instruction to start the measurement operation, the CPU 40 initializes the various constituent elements (step S101). Specifically, the CPU 40 opens the dual-port valve 50 and closes the exhaust valve 32A.

Next, the CPU 40 starts to inflate the pulse wave measurement air bladder 23 and the blood pressure value measurement air bladder 24 by driving the pressure pump 31A (step S102). During the inflation process, the CPU 40 obtains pressure information for calculating blood pressure values such as a maximum blood pressure, a minimum blood pressure, and so on. More specifically, the CPU 40 obtains this pressure information based on a pressure signal inputted from the pressure sensor 33A.

Next, the CPU 40 determines whether or not the blood pressure value measurement has ended (step S103), and in the case where it has been determined that the blood pressure value measurement has ended (YES in step S103), the CPU 40 commences pulse wave measurement (step S104). Specifically, the CPU 40 stops driving the pressure pump 31A and closes the dual-port valve 50. As a result, the internal pressure of the pulse wave measurement air bladder 23 and the internal pressure of the blood pressure value measurement air bladder 24 are each held at a higher pressure than the maximum blood pressure, thus blocking the blood from flowing through the artery in the fitting area of the upper arm; a pulse wave transmitted through the hypodermal tissue from the portion adjacent the blocked artery that is the portion of the cuff on the side closer to the heart is carefully monitored through the low-capacity pulse wave measurement air bladder 23. In this state, the CPU 40 obtains the pulse wave based on the signal inputted from the pressure sensor 33B.

Next, the CPU 40 determines whether or not the pulse wave measurement has ended (step S105), and in the case where it has been determined that the pulse wave measurement has ended (YES in step S105), the CPU 40 moves to a stopping operation (step S106). Specifically, the CPU 40 opens the dual-port valve 50 and opens the exhaust valve 32A.

Next, the CPU 40 calculates a blood pressure value and analyzes the pulse wave (step S107). Specifically, the CPU 40 calculates the maximum blood pressure, the minimum blood pressure, and the index indicating the artery hardness based on the obtained pressure information and pulse wave.

Next, the CPU 40 displays the calculated maximum blood pressure, minimum blood pressure, and index indicating the artery hardness in the display unit 42 (step S108). At this time, the CPU 40 may also output those measurement results to the memory unit 41 and store the results in the memory unit 41. After the measurement results have been displayed, the cuff 20A is removed from the upper arm of the measurement subject.

Through this, the series of measurement operations ends, and the measurement of the various types of blood pressure information using the blood pressure information measurement device 1 according to the present embodiment ends.

With the blood pressure information measurement device 1 and the cuff 20A provided therein according to the present embodiment, as described above, one end of the pulse wave measurement air bladder 23 in the wrapping direction is anchored to the blood pressure value measurement air bladder 24 and rendered immobile, and the portion of the pulse wave measurement air bladder 23 aside from the stated end is not anchored to the blood pressure value measurement air bladder 24 and is thus capable of moving along the stated wrapping direction. Accordingly, wrinkles are effectively suppressed from appearing in the surface of the pulse wave measurement air bladder 23 when the cuff 20A is fitted to the upper arm. The reason why employing this configuration effectively suppresses the appearance of wrinkles will be described in detail hereinafter.

Figure 8A:
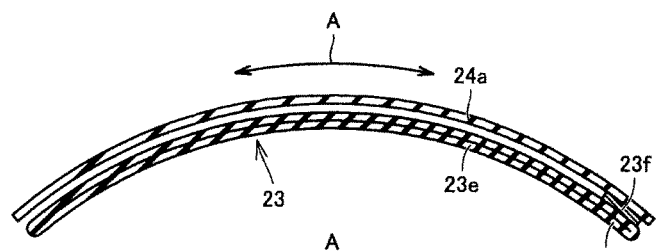
FIGS. 8A and 8B are schematic diagrams illustrating a reason why the blood pressure information measurement device cuff according to the first embodiment of the present invention inhibits the appearance of wrinkles in an air bladder.
Figure 8B:
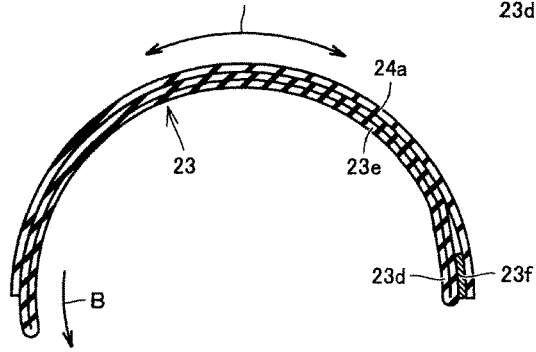
Figure 9A:
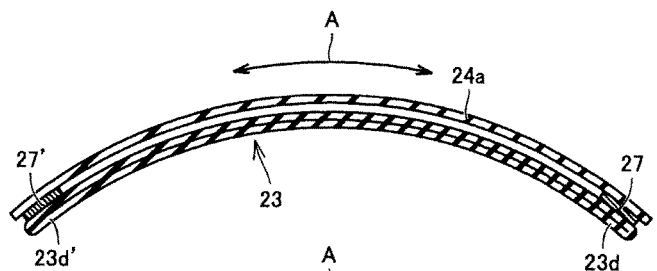
FIGS. 9A and 9B are schematic diagrams used for comparative purposes, to illustrate a reason why the blood pressure information measurement device cuff according to the first embodiment of the present invention inhibits the appearance of wrinkles in an air bladder.
Figure 9B:
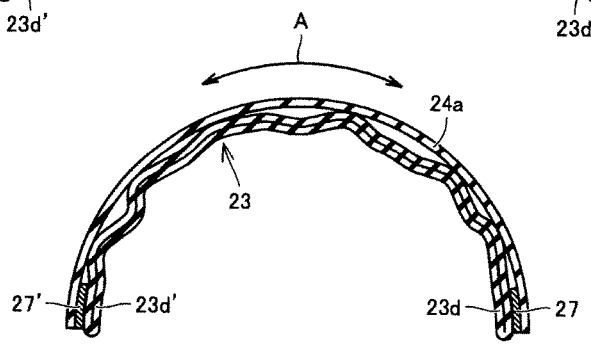

FIGS. 8A and 8B are schematic diagrams illustrating a reason why the blood pressure information measurement device cuff according to the present embodiment inhibits the appearance of wrinkles in the air bladder; FIG. 8A is a schematic cross-sectional view of the cuff before wrapping, whereas FIG. 8B is a schematic cross-sectional view of the cuff during the wrapping process. FIGS. 9A and 9B, meanwhile, are schematic diagrams used for comparative purposes, to illustrate a reason why the blood pressure information measurement device cuff according to the present embodiment inhibits the appearance of wrinkles in the air bladder; FIG. 9A is a schematic cross-sectional view of the cuff before wrapping according to a comparative example, whereas FIG. 9B is a schematic cross-sectional view of the cuff during the wrapping process according to a comparative example. Note that in FIGS. 8A through 9B, the portions aside from the pulse wave measurement air bladder 23, the adhesive member 27, and the inner circumferential portion 24a of the blood pressure value measurement air bladder 24 are not shown.

First, as shown in FIG. 9A, with the cuff according to the comparative example, both ends of the pulse wave measurement air bladder 23 in the wrapping direction (this corresponds to the direction indicated by the arrow A in FIG. 9A) are anchored to the blood pressure value measurement air bladder 24 and are thus rendered immobile. To be more specific, one end of the pulse wave measurement air bladder 23 in the wrapping direction is anchored to the inner circumferential portion 24a of the blood pressure value measurement air bladder 24 using the adhesive member 27, and thus serves as the anchored portion 23d, whereas the other end of the pulse wave measurement air bladder 23 in the wrapping direction is anchored to the inner circumferential portion 24a of the blood pressure value measurement air bladder 24 using the adhesive member 27', and thus serves as the anchored portion 23d'.

As shown in FIG. 9B, in the case where the cuff according to the comparative example has been caused to contract in order to wrap the cuff around the upper arm, the pulse wave measurement air bladder 23 will also take on an overall curved shape based on the bending of the curler 26 (not shown). At this time, because both ends of the pulse wave measurement air bladder 23 are anchored to the blood pressure value measurement air bladder 24 and are thus restricted, areas of excess are created in the pulse wave measurement air bladder 23 that is located further inside than the blood pressure value measurement air bladder 24 when the pulse wave measurement air bladder 23 contracts; because there is nowhere for the areas of excess to escape, the pulse wave measurement air bladder 23 becomes rippled, as illustrated in FIG. 9B. If the cuff is wrapped around the upper arm in this state, the rippled portion of the pulse wave measurement air bladder 23 will be pressed toward the upper arm as-is, and those ripples will result in wrinkles appearing in the surface of the pulse wave measurement air bladder 23.

On the other hand, as shown in FIG. 8A, with the cuff 20A according to the present embodiment, only one end of the pulse wave measurement air bladder 23 in the wrapping direction (this corresponds to the direction indicated by the arrow A in FIG. 8A) is anchored to the blood pressure value measurement air bladder 24 and thus rendered immobile, and the portion aside from that one end is not anchored to the blood pressure value measurement air bladder 24 and is thus capable of movement. To be more specific, the one end of the pulse wave measurement air bladder 23 in the wrapping direction is anchored to the inner circumferential portion 24a of the blood pressure value measurement air bladder 24 using the adhesive member 27, and thus serves as the anchored portion 23d, whereas the portion aside from the one end is simply laid upon the inner circumferential portion 24a of the blood pressure value measurement air bladder 24, and thus serves as the mobile portion 23e.

As shown in FIG. 8B, in the case where the cuff 20A according to the present embodiment has been caused to contract in order to wrap the cuff 20A around the upper arm, the pulse wave measurement air bladder 23 will also take on an overall curved shape based on the bending of the curler 26 (not shown). At this time, because the mobile portion 23e of the pulse wave measurement air bladder 23 is simply laid upon the blood pressure value measurement air bladder 24, the mobile portion 23e slides along the wrapping direction in the direction of the arrow B shown in FIG. 8B with the anchored portion 23d serving as a base point of the sliding movement, and thus the area of excess is not produced in the pulse wave measurement air bladder 23. Accordingly, when the cuff is wrapped around the upper arm in the state, the pulse wave measurement air bladder 23 is held between the blood pressure value measurement air bladder 24 and the upper arm with no ripples being formed in the pulse wave measurement air bladder 23, which inhibits wrinkles from appearing in the surface of the pulse wave measurement air bladder 23.

In this manner, by employing the blood pressure information measurement device cuff 20A and the blood pressure information measurement device 1 according to the present embodiment as described thus far, it is possible to provide a blood pressure information measurement device cuff and a blood pressure information measurement device provided with such a cuff that are capable of effectively suppressing the appearance of wrinkles in the pulse wave measurement air bladder 23 using a simple configuration. Accordingly, it is possible not only to prevent blood stasis caused by wrinkles that have appeared but also to uniformly pressurize an artery in a stable manner and with certainty without differences in the shape of the fitting area to which the cuff 20A is affixed and so on having an effect on that pressurization, which in turn makes it possible to measure various types of blood pressure information, including pulse waves, an index indicating artery hardness, and so on, with a high level of precision.

Figure 10:
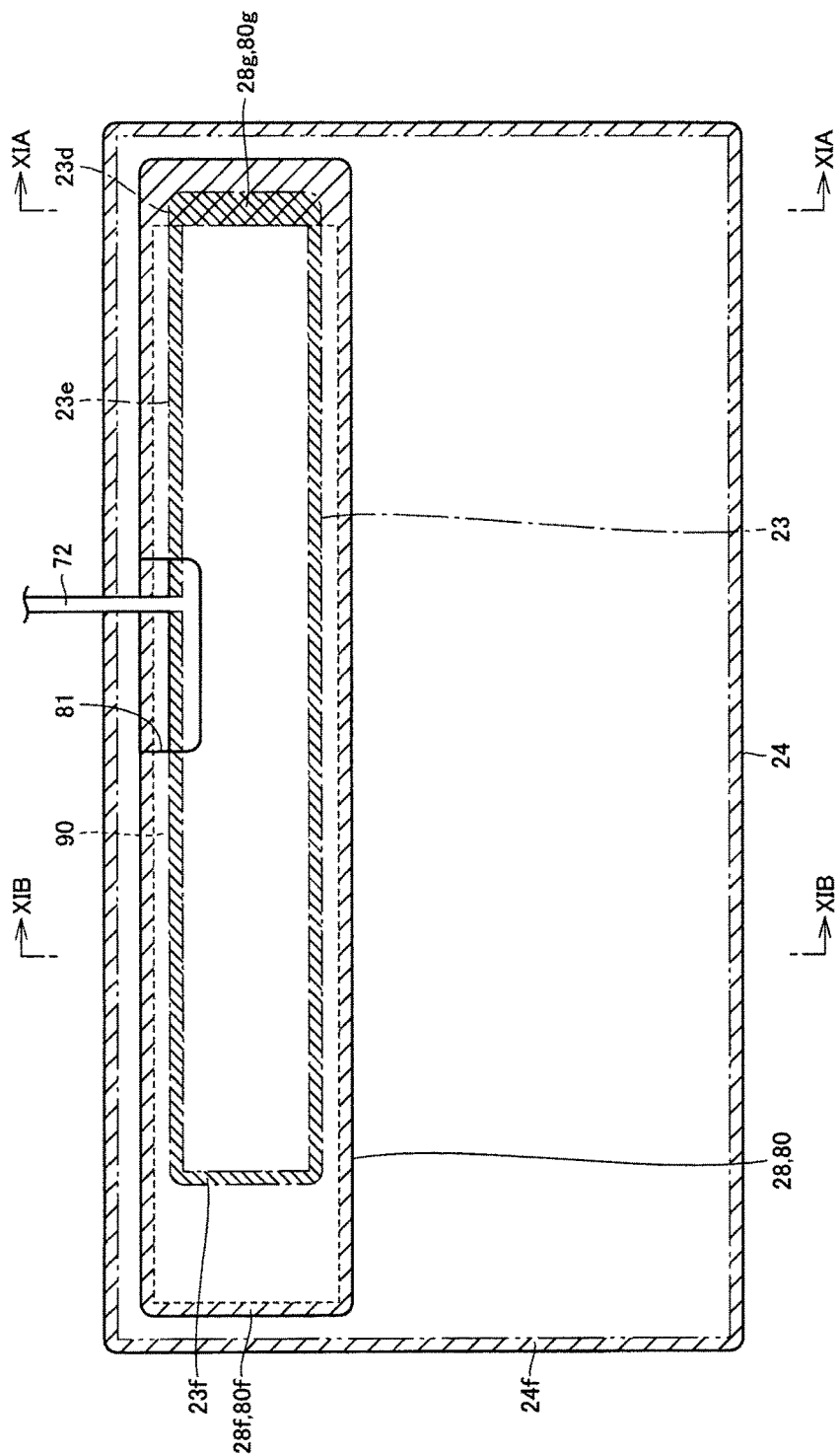
FIG. 10 is a plan view illustrating the configurations of air bladders in a blood pressure information measurement device cuff according to a first variation on the first embodiment of the present invention.
Figure 11A:
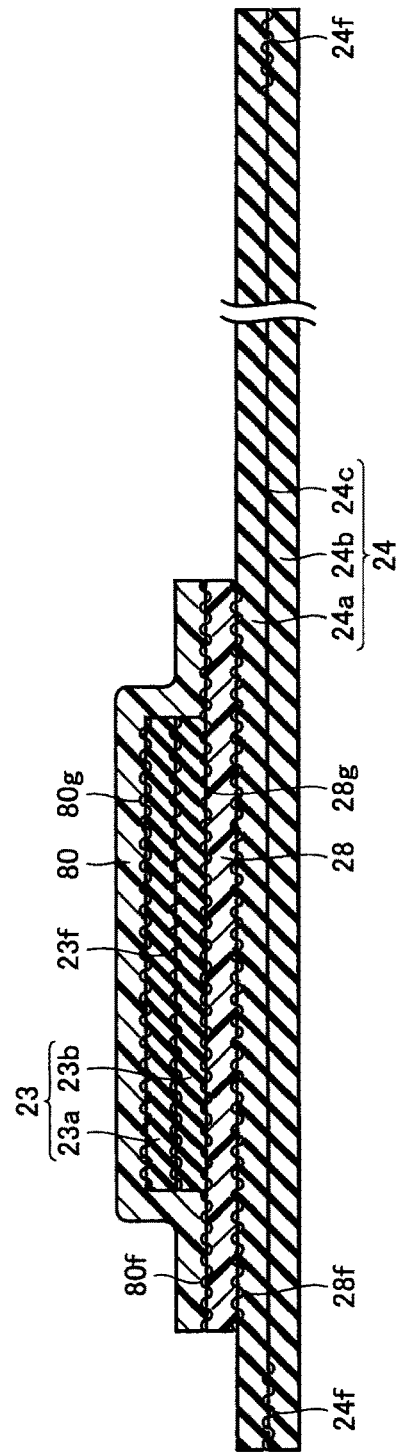
FIG. 11A is a schematic cross-sectional view illustrating the configurations of the air bladders in the blood pressure information measurement device cuff according to the first variation on the first embodiment of the present invention (that is, a schematic cross-sectional view taken along the XIA-XIA line shown in FIG. 10).
Figure 11B:
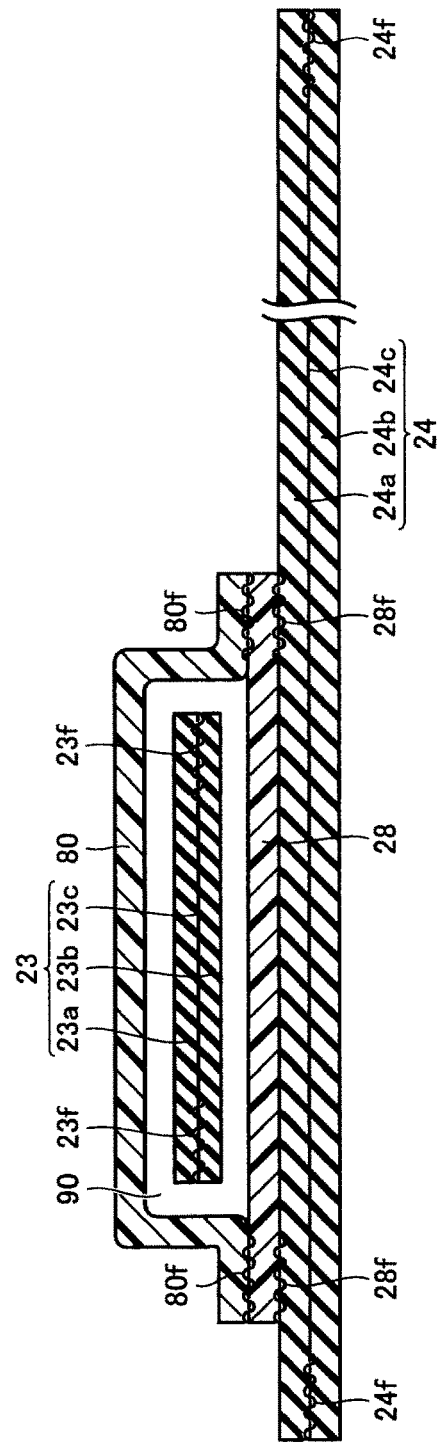
FIG. 11B is a schematic cross-sectional view illustrating the configurations of the air bladders in the blood pressure information measurement device cuff according to the first variation on the first embodiment of the present invention (that is, a schematic cross-sectional view taken along the XIB-XIB line shown in FIG. 10).

FIG. 10 is a plan view illustrating the configurations of air bladders in a blood pressure information measurement device cuff according to a first variation on the present embodiment. Meanwhile, FIG. 11A is a schematic cross-sectional view, illustrating the configurations of the air bladders in the blood pressure information measurement device cuff according to this variation, taken along the XIA-XIA line shown in FIG. 10, whereas FIG. 11B is a schematic cross-sectional view taken along the XIB-XIB line shown in FIG. 10. Hereinafter, the configurations of the air bladders in the blood pressure information measurement device cuff according to the first variation on the present embodiment will be described with reference to FIGS. 10, 11A, and 11B.

As shown in FIG. 10, the configurations of the air bladders in the blood pressure information measurement device cuff according to the present first variation of one or more embodiments of the present invention employ a dual-air bladder configuration in which the pulse wave measurement air bladder 23 and the blood pressure value measurement air bladder 24 are layered, as is used in the blood pressure information measurement device cuff according to the aforementioned present embodiment. In other words, although with the blood pressure information measurement device 1 and the cuff 20A provided therein according to the present embodiment described above, one end of the pulse wave measurement air bladder 23 is anchored to the blood pressure value measurement air bladder 24 using the adhesive member 27 as an example, with the dual air bladders according to the present first variation, welding is used to simplify the configuration even more. Note that in FIG. 10, only the second pipe unit 72 connected to the pulse wave measurement air bladder 23 is shown, and the first pipe unit 71 connected to the blood pressure value measurement air bladder 24 is not shown.

As shown in FIGS. 10, 11A, and 11B, with the dual air bladder configuration according to the present first variation, an intermediate sheet 28 serving as a vibration blocking member, the pulse wave measurement air bladder 23, and a cover sheet 80 serving as a guidance member are stacked in that order upon the exposed surface of the inner circumferential portion 24a of the blood pressure value measurement air bladder 24 (that is, the main surface located toward the body when the cuff is fitted), and by welding predetermined areas of those constituent elements together, the blood pressure value measurement air bladder 24, the intermediate sheet 28, the pulse wave measurement air bladder 23, and the cover sheet 80 are integrated into a single entity, and furthermore, one end of the pulse wave measurement air bladder 23 in the wrapping direction is anchored to the blood pressure value measurement air bladder 24 in an immobile state. Here, according to one or more embodiments of the present invention, a nonwoven urethane sheet having a band shape is used as both the intermediate sheet 28 and the cover sheet 80 in order to make it possible for those constituent elements to be welded to the pulse wave measurement air bladder 23 and the blood pressure value measurement air bladder 24.

To be more specific, the intermediate sheet 28 is aligned upon the inner circumferential portion 24a of the blood pressure value measurement air bladder 24 and the edge thereof is then welded to the inner circumferential portion 24a of the blood pressure value measurement air bladder 24, whereas the cover sheet 80 is aligned upon the intermediate sheet 28 that has been welded to the inner circumferential portion 24a of the blood pressure value measurement air bladder 24, after which a predetermined area of the edge of the cover sheet 80 is welded to the intermediate sheet 28. Meanwhile, the pulse wave measurement air bladder 23 is disposed so that the mobile portion 23e thereof is inserted into a channel 90 defined by the intermediate sheet 28 and the cover sheet 80, and one end thereof in the wrapping direction is welded to the intermediate sheet 28 and the cover sheet 80 and thus serves as the anchored portion 23d.

In addition, a cutout portion 81 is provided in the portion of the cover sheet 80 that corresponds to the portion of the pulse wave measurement air bladder 23 to which the second pipe unit 72 is connected, and the second pipe unit 72 is led to the exterior of the cover sheet 80 via this cutout portion 81. Note that the cutout portion 81 is set to a size that takes into consideration the movement of the mobile portion 23e of the pulse wave measurement air bladder 23 in the wrapping direction.

Through this, the anchored portion 23d of the pulse wave measurement air bladder 23 is anchored to the blood pressure value measurement air bladder 24 using the intermediate sheet 28 and is thus rendered immobile, whereas the mobile portion 23e of the pulse wave measurement air bladder 23 is inserted into the stated channel 90 and is capable of moving along the wrapping direction. Note that in the aforementioned configuration, the intermediate sheet 28 that serves as a vibration blocking member functions as a vibration blocking portion that prevents vibrations from being transmitted, whereas the cover sheet 80 that serves as a guidance member functions as a guidance portion that guides the movement of the mobile portion 23e of the pulse wave measurement air bladder 23.

Note that in FIGS. 10 through 11B, the area where the blood pressure value measurement air bladder 24 and the intermediate sheet 28 are welded together is indicated by the reference numeral 28f, whereas the area where the intermediate sheet 28 and the cover sheet 80 are welded together is indicated by the reference numeral 80f. Likewise, in FIGS. 10 through 11B, the area where the pulse wave measurement air bladder 23 and the intermediate sheet 28 are welded together is indicated by the reference numeral 28g, whereas the area where the pulse wave measurement air bladder 23 and the cover sheet 80 are welded together is indicated by the reference numeral 80g. Furthermore, in FIGS. 10 through 11B, the area where the inner circumferential portion 23a and the outer circumferential portion 23b of the pulse wave measurement air bladder 23 are welded together is indicated by the reference numeral 23f, whereas the area where the inner circumferential portion 24a and the outer circumferential portion 24b of the blood pressure value measurement air bladder 24 are welded together is indicated by the reference numeral 24f.

When manufacturing such a dual air bladder configuration, first, the pulse wave measurement air bladder 23 is formed by overlapping resin sheets that serve as the inner circumferential portion 23a and the outer circumferential portion 23b of the pulse wave measurement air bladder 23 and then welding the edges of those sheets together. Next, the intermediate sheet 28 and the cover sheet 80 are overlaid upon the pulse wave measurement air bladder 23, and the edges thereof are welded. At this time, one end of the pulse wave measurement air bladder 23 (that is, the portion that serves as the anchored portion 23d) is welded to both the intermediate sheet 28 and the cover sheet 80, whereas the portion aside from the one end of the pulse wave measurement air bladder 23 (that is, the portion that serves as the mobile portion 23e) is inserted into the channel 90 defined by the intermediate sheet 28 and the cover sheet 80. Then, the subassembly configured by integrating the pulse wave measurement air bladder 23, the intermediate sheet 28, and the cover sheet 80 is overlaid upon the inner circumferential portion 24a of the blood pressure value measurement air bladder 24, and the edges thereof are welded. After this, the outer circumferential portion 24b is overlaid on the inner circumferential portion 24a of the blood pressure value measurement air bladder 24 to which the stated subassembly has been welded, and the edges thereof are welded; this completes the stated dual air bladder configuration.

By employing the dual air bladder configuration according to the present first variation as described thus far, it is possible to effectively suppress the appearance of wrinkles in the pulse wave measurement air bladder 23 using an extremely simple configuration. Furthermore, by employing the dual air bladder configuration according to the present first variation, the configuration can be manufactured with ease using a simple operation in which the welding operations described thus far are simply repeated multiple times, which makes it possible to manufacture the blood pressure information measurement device cuff at a low cost.

Figure 12:
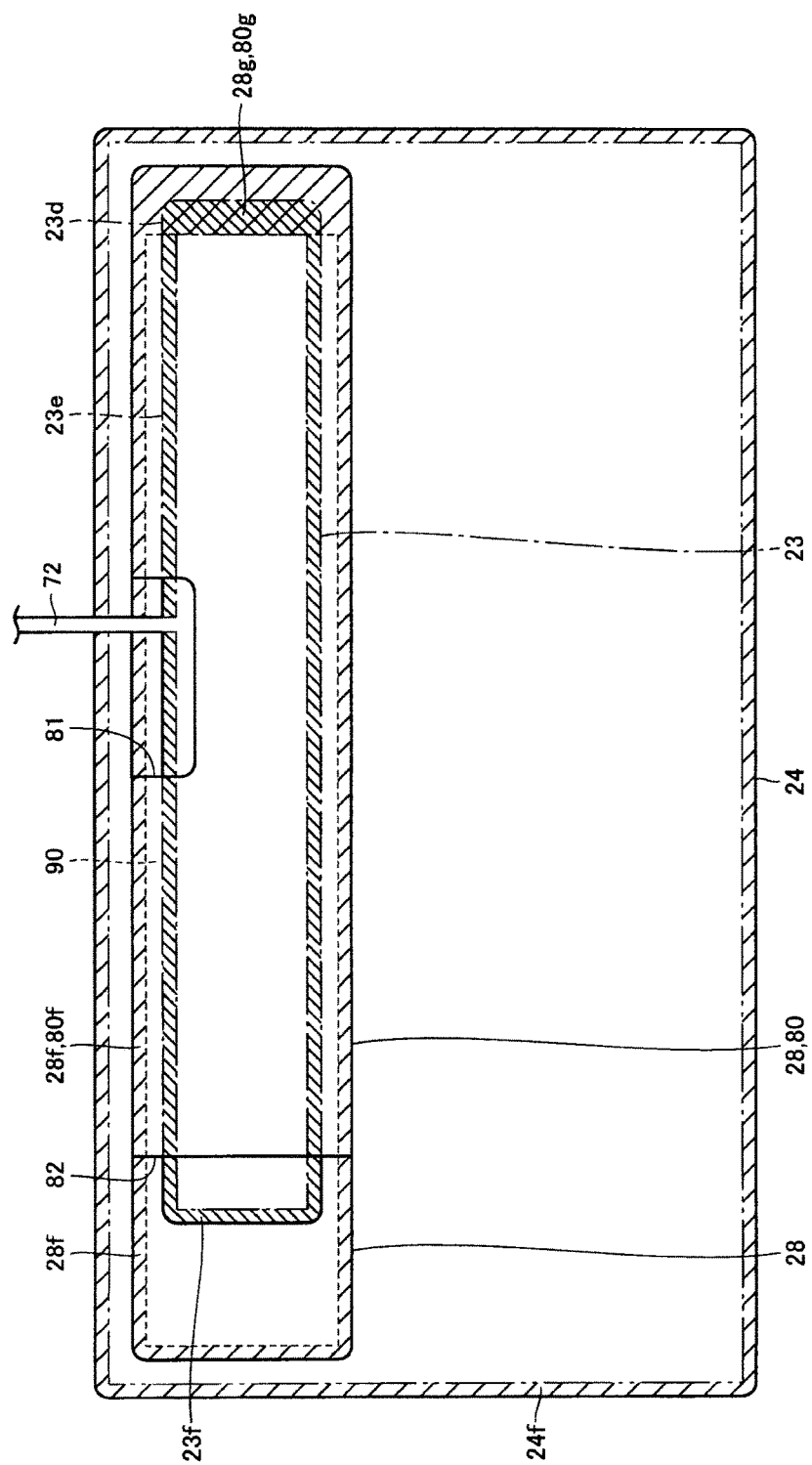
FIG. 12 is a plan view illustrating the configuration of an air bladder in a blood pressure information measurement device cuff according to a second variation on the first embodiment of the present invention.

FIG. 12 is a plan view illustrating the configurations of air bladders in a blood pressure information measurement device cuff according to a second variation on the present embodiment. Hereinafter, the configurations of the air bladders in the blood pressure information measurement device cuff according to the second variation on the present embodiment will be described with reference to FIG. 12.

As shown in FIG. 12, the configuration of the air bladder in the blood pressure information measurement device cuff according to the present second variation is basically the same as the configuration of the air bladder in the blood pressure information measurement device cuff according to the first variation on the present embodiment described above; the only difference is that one end in the wrapping direction of the cover sheet 80 that serves as a guidance member is open, without being welded to the intermediate sheet 28, and thus serves as an open end 82, and the end of the pulse wave measurement air bladder 23 on the opposite side as the side on which the anchored portion 23d is located is led out to the exterior from the open end 82.

By employing the dual air bladder configuration according to the present second variation as described thus far, the same effects as when employing the dual air bladder configuration according to the first variation on the present embodiment described above can be achieved; furthermore, because part of the mobile portion 23e of the pulse wave measurement air bladder 23 can enter and exit from the open end 82, the movement of the mobile portion 23e of the pulse wave measurement air bladder 23 is not regulated by the channel 90, which makes it possible to ensure a greater movement range for the mobile portion 23e.

Second Embodiment

Figure 13:
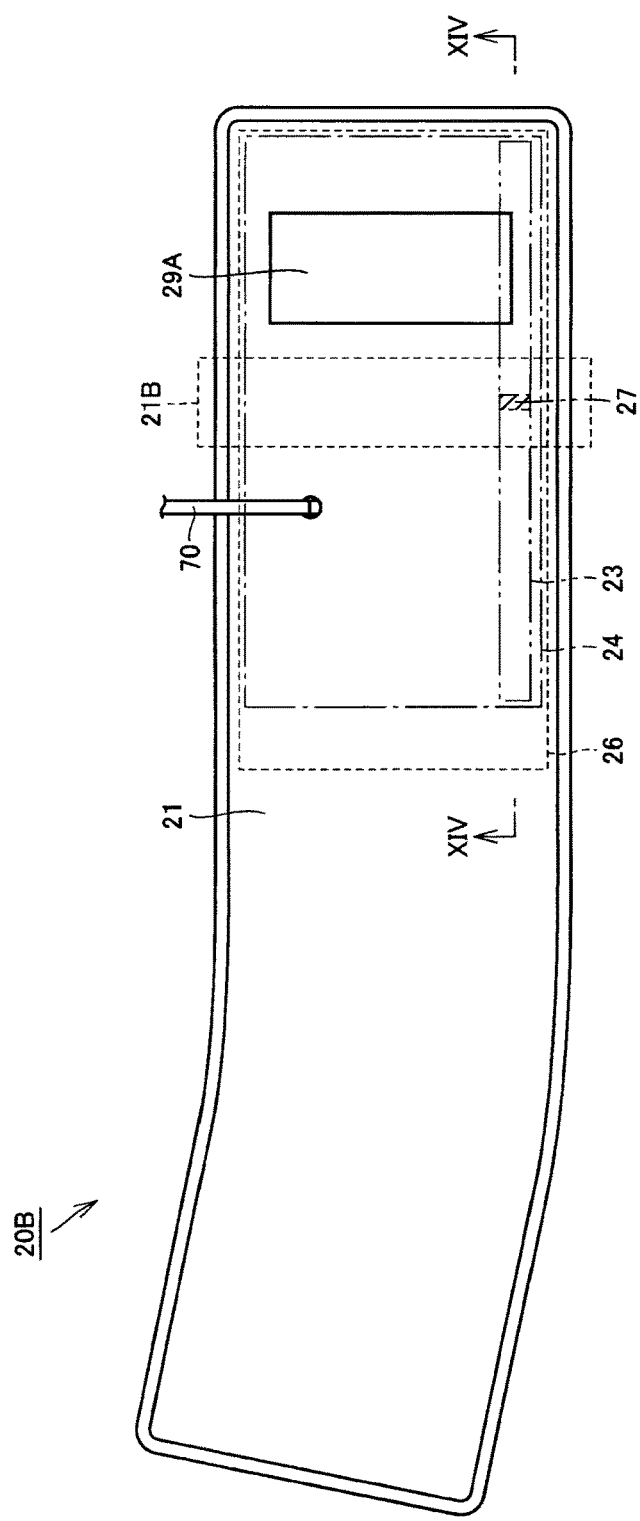
FIG. 13 is a diagram illustrating a blood pressure information measurement device cuff according to a second embodiment of the present invention in an unwrapped state, as seen from the outer circumferential surface thereof.
Figure 14:
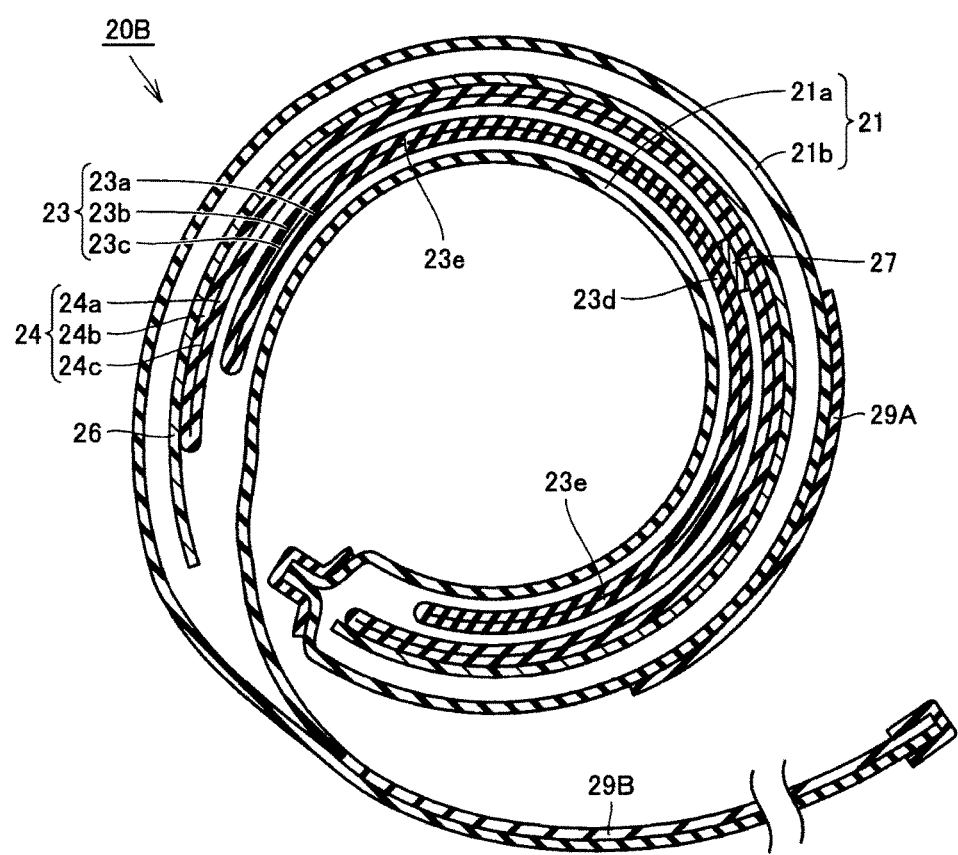
FIG. 14 is a cross-sectional view illustrating the blood pressure information measurement device cuff according to the second embodiment of the present invention from a plane orthogonal to the axial direction of the cuff.

FIG. 13 is a diagram illustrating a blood pressure information measurement device cuff according to a second embodiment of the present invention in an unwrapped state, as seen from the outer circumferential surface thereof. FIG. 14, meanwhile, is a cross-sectional view illustrating a plane orthogonal to the axial direction of the cuff shown in FIG. 13. Here, the cross-section shown in FIG. 14 is a cross-section of an area that includes a pulse wave measurement air bladder, and is taken along the XIV-XIV line shown in FIG. 13, which shows the cuff in an unwrapped state. The structure of the blood pressure information measurement device cuff according to the present embodiment will be described with reference to FIGS. 13 and 14.

A cuff 20B according to the present embodiment is provided in the blood pressure information measurement device 1 described in the aforementioned first embodiment of the present invention, and the difference between the cuff 20B and the cuff 20A according to the aforementioned first embodiment lies in the location at which the pulse wave measurement air bladder 23 is anchored to the blood pressure value measurement air bladder 24. Specifically, as shown in FIGS. 13 and 14, with the cuff 20B according to the present embodiment, what is approximately the center of the pulse wave measurement air bladder 23 in the wrapping direction relative to the upper arm is anchored to the blood pressure value measurement air bladder 24 using the adhesive member 27, and the portion aside from the stated approximate center is not anchored to the blood pressure value measurement air bladder 24. Accordingly, the approximate center of the pulse wave measurement air bladder 23 that is anchored to the blood pressure value measurement air bladder 24 via the adhesive member 27 functions as the anchored portion 23d that cannot be moved relative to the blood pressure value measurement air bladder 24, and the portions of the pulse wave measurement air bladder 23 aside from the stated approximate center that are not anchored to the blood pressure value measurement air bladder 24 function as the mobile portions 23e that can be moved relative to the blood pressure value measurement air bladder 24 along the aforementioned wrapping direction.

In this manner, by employing the cuff 20B and the blood pressure information measurement device 1 provided therewith according to the present embodiment, it is possible to provide a blood pressure information measurement device cuff and a blood pressure information measurement device provided therewith that are capable of effectively suppressing the appearance of wrinkles in the pulse wave measurement air bladder 23 using a simple configuration. In other words, because the pair of mobile portions 23e of the pulse wave measurement air bladder 23 disposed so as to surround the anchored portion 23d are simply laid upon the blood pressure value measurement air bladder 24, the pair of mobile portions 23e slide along the wrapping direction with the anchored portion 23d serving as a base point of the sliding movement, thus preventing the appearance of wrinkles in the pulse wave measurement air bladder 23. Accordingly, it is possible not only to prevent blood stasis caused by wrinkles that have appeared, but also to uniformly pressurize an artery in a stable manner and with certainty without differences in the shape of the fitting area to which the cuff 20B is affixed and so on having an effect on that pressurization, which in turn makes it possible to measure various types of blood pressure information, including pulse waves, an index indicating artery hardness, and so on, with a high level of precision.

Figure 15:
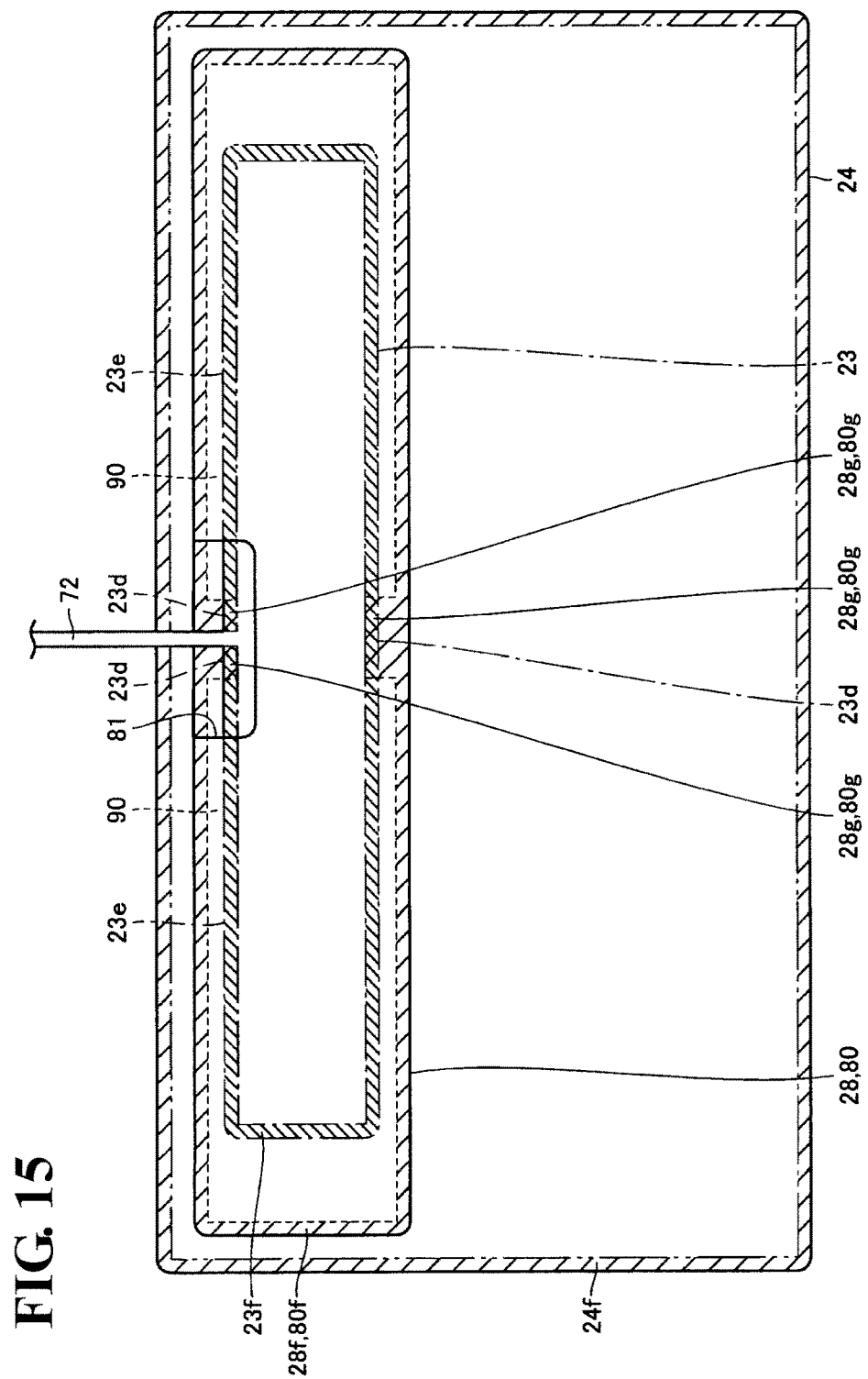
FIG. 15 is a plan view illustrating the configuration of an air bladder in a blood pressure information measurement device cuff according to a first variation on the second embodiment of the present invention.

FIG. 15 is a plan view illustrating the configurations of air bladders in a blood pressure information measurement device cuff according to a first variation on the present embodiment. Hereinafter, the configurations of the air bladders in the blood pressure information measurement device cuff according to the first variation on the present embodiment will be described with reference to FIG. 15.

As shown in FIG. 15, the configurations of the air bladders in the blood pressure information measurement device cuff according to the present first variation of one or more embodiments of the present invention employ a dual air bladder configuration in which the pulse wave measurement air bladder 23 and the blood pressure value measurement air bladder 24 are layered, as is used in the blood pressure information measurement device cuff according to the aforementioned present embodiment. In other words, although with cuff 20B according to the present embodiment described above, the approximate center of the pulse wave measurement air bladder 23 is anchored to the blood pressure value measurement air bladder 24 using the adhesive member 27 as an example, with the dual air bladders according to the present first variation, welding is used to simplify the configuration even more. Note that in FIG. 15, only the second pipe unit 72 connected to the pulse wave measurement air bladder 23 is shown, and the first pipe unit 71 connected to the blood pressure value measurement air bladder 24 is not shown.

As shown in FIG. 15, with the dual air bladder configuration according to the present first variation, the intermediate sheet 28 serving as a vibration blocking member, the pulse wave measurement air bladder 23, and the cover sheet 80 serving as a guidance member are stacked in that order upon the exposed surface of the inner circumferential portion 24a of the blood pressure value measurement air bladder 24 (that is, the main surface located toward the body when the cuff is fitted), and by welding predetermined areas of those constituent elements together, the blood pressure value measurement air bladder 24, the intermediate sheet 28, the pulse wave measurement air bladder 23, and the cover sheet 80 are integrated into a single entity, and furthermore, the approximate center of the pulse wave measurement air bladder 23 in the wrapping direction is anchored to the blood pressure value measurement air bladder 24 in an immobile state. Here, according to one or more embodiments of the present invention, a nonwoven urethane sheet having a band shape is used as both the intermediate sheet 28 and the cover sheet 80 in order to make it possible for those constituent elements to be welded to the pulse wave measurement air bladder 23 and the blood pressure value measurement air bladder 24.

To be more specific, the intermediate sheet 28 is aligned upon the inner circumferential portion 24a of the blood pressure value measurement air bladder 24 and the edge thereof is then welded to the inner circumferential portion 24a of the blood pressure value measurement air bladder 24, whereas the cover sheet 80 is aligned upon the intermediate sheet 28 that has been welded to the inner circumferential portion 24a of the blood pressure value measurement air bladder 24, after which a predetermined area of the edge of the cover sheet 80 is welded to the intermediate sheet 28. In addition, the pulse wave measurement air bladder 23 is disposed so that each in the pair of mobile portions 23e is inserted into a corresponding channel 90 defined by the intermediate sheet 28 and the cover sheet 80, and the approximate center in the wrapping direction thereof is welded to the intermediate sheet 28 and the cover sheet 80 and thus serves as the anchored portion 23d.

Meanwhile, the second pipe unit 72 is connected to the pulse wave measurement air bladder 23 in the vicinity of the stated anchored portion 23d, and the cutout portion 81 is provided in the cover sheet 80 in the area at which the second pipe unit 72 is located.

Through this, the anchored portion 23d of the pulse wave measurement air bladder 23 is anchored to the blood pressure value measurement air bladder 24 using the intermediate sheet 28 and is thus rendered immobile, whereas the pair of mobile portions 23e of the pulse wave measurement air bladder 23 are inserted into the stated corresponding channels 90 and are capable of moving along the wrapping direction. Note that in the aforementioned configuration, the intermediate sheet 28 that serves as a vibration blocking member functions as a vibration blocking portion that prevents vibrations from being transmitted, whereas the cover sheet 80 that serves as a guidance member functions as a guidance portion that guides the movement of the pair of mobile portions 23e of the pulse wave measurement air bladder 23.

Note that in FIG. 15, the area where the blood pressure value measurement air bladder 24 and the intermediate sheet 28 are welded together is indicated by the reference numeral 28f, whereas the area where the intermediate sheet 28 and the cover sheet 80 are welded together is indicated by the reference numeral 80f. Likewise, in FIG. 15, the area where the pulse wave measurement air bladder 23 and the intermediate sheet 28 are welded together is indicated by the reference numeral 28g, whereas the area where the pulse wave measurement air bladder 23 and the cover sheet 80 are welded together is indicated by the reference numeral 80g. Furthermore, in FIG. 15, the area where the inner circumferential portion 23a and the outer circumferential portion 23b of the pulse wave measurement air bladder 23 are welded together is indicated by the reference numeral 23f, whereas the area where the inner circumferential portion 24a and the outer circumferential portion 24b of the blood pressure value measurement air bladder 24 are welded together is indicated by the reference numeral 24f.

When manufacturing such a dual air bladder configuration, first, the pulse wave measurement air bladder 23 is formed by overlapping resin sheets that serve as the inner circumferential portion 23a and the outer circumferential portion 23b of the pulse wave measurement air bladder 23 and then welding the edges of those sheets together. Next, the intermediate sheet 28 and the cover sheet 80 are overlaid upon the pulse wave measurement air bladder 23, and the edges thereof are welded. At this time, the approximate center of the pulse wave measurement air bladder 23 (that is, the portion that serves as the anchored portion 23d) is welded to both the intermediate sheet 28 and the cover sheet 80, and the portions aside from the stated approximate center of the pulse wave measurement air bladder 23 (that is, the portions that serve as the pair of mobile portions 23e) are inserted into the pair of channels 90 defined by the intermediate sheet 28 and the cover sheet 80. Then, the subassembly configured by integrating the pulse wave measurement air bladder 23, the intermediate sheet 28, and the cover sheet 80 is overlaid upon the inner circumferential portion 24a of the blood pressure value measurement air bladder 24, and the edges thereof are welded. After this, the outer circumferential portion 24b is overlaid on the inner circumferential portion 24a of the blood pressure value measurement air bladder 24 to which the stated subassembly has been welded, and the edges thereof are welded; this completes the stated dual air bladder configuration.

By employing the dual air bladder configuration according to the present first variation as described thus far, it is possible to effectively suppress the appearance of wrinkles in the pulse wave measurement air bladder 23 using an extremely simple configuration. Furthermore, by employing the dual air bladder configuration according to the present first variation, the configuration can be manufactured with ease using a simple operation in which the welding operations described thus far are simply repeated multiple times, which makes it possible to manufacture the blood pressure information measurement device cuff at a low cost.

Figure 16:
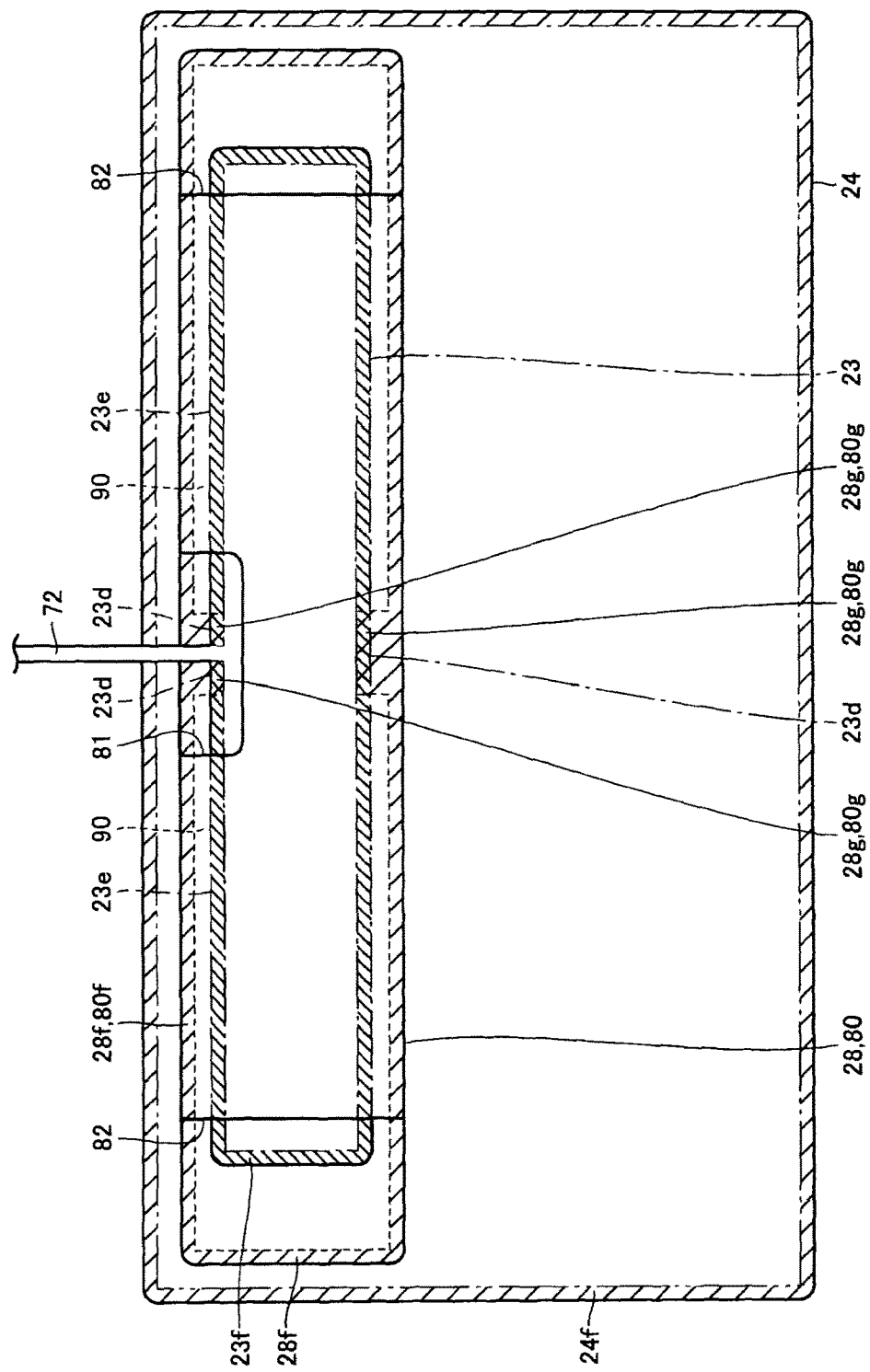
FIG. 16 is a plan view illustrating the configuration of an air bladder in a blood pressure information measurement device cuff according to a second variation on the second embodiment of the present invention.

FIG. 16 is a plan view illustrating the configurations of air bladders in a blood pressure information measurement device cuff according to a second variation on the present embodiment. Hereinafter, the configurations of the air bladders in the blood pressure information measurement device cuff according to the second variation on the present embodiment will be described with reference to FIG. 16.

As shown in FIG. 16, the configuration of the air bladder in the blood pressure information measurement device cuff according to the present second variation is basically the same as the configuration of the air bladder in the blood pressure information measurement device cuff according to the first variation on the present embodiment described above; the only difference is that both ends in the wrapping direction of the cover sheet 80 that serves as a guidance member are open, without being welded to the intermediate sheet 28, and thus serve as a pair of open ends 82, and both ends of the pulse wave measurement air bladder 23 are led out to the exterior from the pair of open ends 82.

By employing the dual air bladder configuration according to the present second variation as described thus far, the same effects as when employing the dual air bladder configuration according to the first variation on the present embodiment described above can be achieved; furthermore, because parts of the pair of mobile portions 23e of the pulse wave measurement air bladder 23 can enter into and exit from the stated pair of open ends 82, the movement of the pair of mobile portions 23e of the pulse wave measurement air bladder 23 is not regulated by the pair of channels 90, which makes it possible to ensure a greater movement range for the pair of mobile portions 23e.

Although the aforementioned first and second embodiments of the present invention and the variations thereon describe examples of a blood pressure information measurement device cuff configured so that a curler serving as a curved elastic board is contained within an outer cover and a blood pressure information measurement device provided with such a cuff, it should be noted that embodiments of the present invention are of course applicable in a blood pressure information measurement device cuff that does not include a curler and in a blood pressure information measurement device provided with such a cuff.

In addition, although the aforementioned first and second embodiments of the present invention and the variations thereon describe examples in which embodiments of the present invention are applied in a blood pressure information measurement device in which the main unit and the cuff are configured of separate units and the main unit and the cuff are connected via a flexible air tube or the like, and in a blood pressure information measurement device cuff provided in such a device, it should be noted that embodiments of the present invention can of course also be applied in a blood pressure information measurement device in which the main unit and the cuff are linked in a movable state (what is known as an automatic wrapping blood pressure information measurement device) and in a blood pressure information measurement device cuff provided in such a device.

In addition, although the aforementioned first and second embodiments of the present invention and the variations thereon describe examples in which embodiments of the present invention are applied in a blood pressure information measurement device cuff in which the upper arm is assigned as the fitting area for the cuff, and in a blood pressure information measurement device provided with such a cuff, it should be noted that embodiments of the present invention can also be applied in any blood pressure information measurement device cuff, and any blood pressure information measurement device provided with such a cuff, that is designed to be fitted on one of the four limbs of the body.

In addition, although the aforementioned first and second embodiments of the present invention and the variations thereon describe examples of a blood pressure information measurement device cuff that employs air bladders into which pressurized air is injected as the pulse wave measurement air bladder and the blood pressure value measurement air bladder, and of a blood pressure information measurement device provided with such a cuff, it should be noted that embodiments of the present invention are not particularly limited to air bladders, and the stated constituent elements can of course be configured of a gas bladder into which another gas is injected, a liquid bladder into which a liquid is injected, or the like.

In addition, although the aforementioned first and second embodiments of the present invention and the variations thereon describe examples in which embodiments of the present invention are applied in a blood pressure information measurement device capable of obtaining a maximum blood pressure, a minimum blood pressure, an index indicating artery hardness, and so on, and in a blood pressure information measurement device cuff provided in such a device, it should be noted that embodiments of the present invention can of course be applied in a device, aside from the stated device, that obtains blood pressure information.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 blood pressure information measurement device
10 main unit
11 casing
20A, 20B cuff
21 outer cover
21A one end
21a inside cover
21b outside cover
23 pulse wave measurement air bladder
23a inner circumferential portion
23b outer circumferential portion
23c inner cavity
23d anchored portion
23e mobile portion
23f welded portion
24 blood pressure value measurement air bladder
24a inner circumferential portion
24b outer circumferential portion
24c inner cavity
24f welded portion
26 curler
27 adhesive member
28 intermediate sheet
28f, 28g welded portion
29A, 29B surface fastener
30A inflation/deflation mechanism
31A pressure pump
32A exhaust valve
33A, 33B pressure sensor
36A pressure pump driving circuit
37A exhaust valve driving circuit
38A, 38B amplifier
39A, 39B A/D converter 40 CPU
41 memory unit
42 display unit
43 operating unit
50 dual-port valve
51 dual-port valve driving circuit
70 air tube
71 first pipe unit
72 second pipe unit
80 cover sheet
80f, 80g welded portion
81 cutout portion
82 open end
90 channel
100 left arm
101 upper arm

The invention claimed is:

1. A blood pressure information measurement device cuff that takes on a ring-shaped state when wrapped around a fitting area in a fitted state, the cuff comprising:
   a first fluid bladder that is configured to be wrapped around the fitting area when in the fitted state, the first fluid bladder having a first length measured in the wrapping direction and a first width measured in a direction perpendicular to the wrapping direction; and
   a second fluid bladder configured to be disposed so as to be closer to the fitting area than the first fluid bladder is when in the fitted state where there is overlap between the first fluid bladder and the second fluid bladder, the second fluid bladder being covered by the first fluid bladder when wrapped around the fitting area, the second fluid bladder having a second length measured in the wrapping direction and a second width measured in the direction perpendicular to the wrapping direction, wherein the second width is less than the first width, and the second length is approximately equal to the first length, and
   wherein the second fluid bladder comprises:
      an anchored portion that is anchored to the first fluid bladder so as to be immobile relative to the first fluid bladder at only one end of the second fluid bladder; and
      a mobile portion that is not anchored to the first fluid bladder so as to be mobile relative to the first fluid bladder along a wrapping direction in which the cuff is wrapped around the fitting area,
   wherein the anchored portion of the second fluid bladder is adjacent the mobile portion, and traverses less than a quarter of the second length of the second fluid bladder at the only one end of the second fluid bladder.

2. The blood pressure information measurement device cuff according to claim 1,
   wherein the first fluid bladder is, when in the fitted state, configured to be wrapped around an area closer to a heart within the fitting area and an area away from the heart within the fitting area, and
   wherein the second fluid bladder is, when in the fitted state, configured to be wrapped around only the area closer to the heart within the fitting area.

3. The blood pressure information measurement device cuff according to claim 1, further comprising:
   a guidance portion that guides a movement of the mobile portion along the wrapping direction.

4. The blood pressure information measurement device cuff according to claim 1, further comprising:
   a vibration blocking portion, disposed between the first fluid bladder and the second fluid bladder, that prevents vibrations produced in the first fluid bladder from being transmitted to the second fluid bladder and that prevents vibrations produced in the second fluid bladder from being transmitted to the first fluid bladder.

5. The blood pressure information measurement device cuff according to claim 1, further comprising:
   a guidance portion that guides the movement of the mobile portion along the wrapping direction; and
   a vibration blocking portion, disposed between the first fluid bladder and the second fluid bladder, that prevents vibrations produced in the first fluid bladder from being transmitted to the second fluid bladder and that prevents vibrations produced in the second fluid bladder from being transmitted to the first fluid bladder,
   wherein the guidance portion and the vibration blocking portion are both configured of a nonwoven material formed into a band shape, and
   wherein the vibration blocking portion is disposed between the first fluid bladder and the second fluid bladder and is anchored to the first fluid bladder, the guidance portion is overlaid upon the vibration blocking portion so as to cover at least part of the second fluid bladder and is anchored to the vibration blocking portion, and the movement of the mobile portion along the wrapping direction is guided by inserting at least part of the mobile portion into a channel defined by the vibration blocking portion and the guidance portion.

6. The blood pressure information measurement device cuff according to claim 5,
   wherein the entirety of the mobile portion is inserted into the channel.

7. The blood pressure information measurement device cuff according to claim 5,
   wherein an end of the mobile portion located on an opposite side as the anchored portion is disposed having been led out from the channel.

8. The blood pressure information measurement device cuff according to claim 5,
   wherein the anchored portion is formed by anchoring one end of the second fluid bladder to the first fluid bladder via the vibration blocking portion.

9. The blood pressure information measurement device cuff according to claim 8,
   wherein the anchoring of the vibration blocking portion to the first fluid bladder, the anchoring of the guidance portion to the vibration blocking portion, and the anchoring of the second fluid bladder to the vibration blocking portion are all carried out through welding.

10. The blood pressure information measurement device cuff according to claim 1,
    wherein the anchored portion is located at one end of the second fluid bladder in a lengthwise direction thereof.

11. The blood pressure information measurement device cuff according to claim 10, further comprising:
    an outer cover that contains the first fluid bladder and the second fluid bladder, the outer cover having two ends, a first end and a second end, in the wrapping direction, wherein the first end of the outer cover is located on an inner side of the cuff when the cuff is wrapped around the fitting area when in the fitted state, and
    wherein the anchored portion is disposed closer to the first end of the outer cover than to the second end of the outer cover.

12. The blood pressure information measurement device cuff according to claim 1, wherein the anchored portion is located in approximately the center of the second fluid bladder in a lengthwise direction thereof.

13. A blood pressure information measurement device comprising:
- the blood pressure information measurement device cuff according to claim 1;
- an inflation/deflation mechanism for inflating and deflating the first fluid bladder and the second fluid bladder;
- a first pressure detection unit, which detects the pressure in the first fluid bladder and produces a first pressure information;
- a second pressure detection unit, which detects the pressure in the second fluid bladder and produces a second pressure information; and
- a blood pressure information calculation unit, which calculates a blood pressure information based on the first pressure information and the second pressure information.

\* \* \* \* \*